(12) United States Patent
Dodds

(10) Patent No.: US 12,364,513 B2
(45) Date of Patent: Jul. 22, 2025

(54) ANCHORING DEVICE FOR USE IN SPINAL DEFORMITY CORRECTION SURGERY

(71) Applicant: Michael Kenneth Dodds, Dublin (IE)

(72) Inventor: Michael Kenneth Dodds, Dublin (IE)

(*) Notice: Subject to any disclaimer, the term of this patent is extended or adjusted under 35 U.S.C. 154(b) by 543 days.

(21) Appl. No.: 17/616,265

(22) PCT Filed: Jun. 5, 2020

(86) PCT No.: PCT/GB2020/051370
§ 371 (c)(1),
(2) Date: Dec. 3, 2021

(87) PCT Pub. No.: WO2020/245603
PCT Pub. Date: Dec. 10, 2020

(65) Prior Publication Data
US 2022/0313319 A1     Oct. 6, 2022

(30) Foreign Application Priority Data
Jun. 6, 2019 (GB) ..................... 1908098

(51) Int. Cl.
*A61B 17/70* (2006.01)
*A61B 17/80* (2006.01)

(52) U.S. Cl.
CPC ...... *A61B 17/7022* (2013.01); *A61B 17/7034* (2013.01); *A61B 17/7044* (2013.01);
(Continued)

(58) Field of Classification Search
CPC ............ A61B 17/7022; A61B 17/7053; A61B 17/7001; A61B 17/7035; A61B 17/7037; A61B 17/7032; A61B 17/7034
See application file for complete search history.

(56) References Cited

U.S. PATENT DOCUMENTS

| 2011/0093015 A1 | 4/2011 | Ramsay et al. |
| 2012/0029567 A1* | 2/2012 | Zolotov ............... A61B 17/705 606/264 |

(Continued)

FOREIGN PATENT DOCUMENTS

| EP | 2 777 569 | 9/2014 |
| GB | 2381197 | 4/2003 |

(Continued)

OTHER PUBLICATIONS

Intellectual Property Office, Search Report, App. No. GB1908098.5 (Nov. 26, 2019).

(Continued)

*Primary Examiner* — Ellen C Hammond
(74) *Attorney, Agent, or Firm* — Walters & Wasylyna LLC

(57) ABSTRACT

An anchoring device (40) for anchoring one or more sub-laminar bands or tapes (60a, 60b) to a pedicle screw (30), the device (40) comprising: a first portion (41) configured for attachment to at least a base portion (32 L) of a head portion (32) of the pedicle screw (32); and at least one second portion (46a, 46b) for anchoring thereto a or a respective sub-laminar band or tape (60a, 60b); wherein the first portion (41) includes first interengagement means (42Na, 42 Nb) for interengagement with corresponding notches or recesses (32Na, 32 Nb) in the head portion (32) of the pedicle screw (32) to effect the said attachment of the first portion (41) of the anchoring device (40) thereto.

19 Claims, 13 Drawing Sheets

(52) U.S. Cl.
CPC ........ *A61B 17/7053* (2013.01); *A61B 17/707* (2013.01); *A61B 17/8047* (2013.01)

(56) References Cited

U.S. PATENT DOCUMENTS

| | | |
|---|---|---|
| 2019/0192190 A1 | 6/2019 | Gray et al. |
| 2019/0290334 A1 | 9/2019 | Prygoski et al. |

FOREIGN PATENT DOCUMENTS

| | | |
|---|---|---|
| WO | WO 2012/138444 | 10/2012 |
| WO | WO 2013/036279 | 3/2013 |
| WO | WO 2014/052944 | 4/2014 |
| WO | WO 2016/166448 | 10/2016 |
| WO | WO 2016/166482 | 10/2016 |

OTHER PUBLICATIONS

Intellectual Property Office, Search Report, App. No. GB2008508.0 (Nov. 23, 2020).

International Searching Authority: International Search Report and Written Opinion, Intl. App. No. PCT/GB2020/051370 (Oct. 6, 2020).

* cited by examiner

ANCHORING DEVICE FOR USE IN SPINAL DEFORMITY CORRECTION SURGERY

TECHNICAL FIELD

This application is the U.S. national phase entry of Intl. App. No. PCT/GB2020/051370 filed on Jun. 5, 2020, which claims priority from GB1908098.5 filed on Jun. 6, 2019. The entire contents of PCT/GB2020/051370 and GB1908098.5 are incorporated herein by reference.

This invention relates to an anchoring device for use in spinal deformity correction surgery. More particularly, though not exclusively, the invention relates to an anchoring device for use with a pedicle screw, especially by attachment to a pedicle screw, to provide a system for enhanced anchoring of sub-laminar bands used in corrective spinal vertebral fixation surgery. The invention further relates to such anchoring device and pedicle screw combinations, to a pedicle screw for use with such an anchoring device, and to methods of use of such anchoring devices and anchoring device-and-pedicle screw combinations in spinal deformity correction surgery.

BACKGROUND OF THE INVENTION AND PRIOR ART

Scoliosis is a common form of spinal deformity. Surgical correction of the deformity generally involves the implantation of fixation anchors onto plural vertebrae, which are then drawn onto a stabilising rod, resulting in partial correction of the deformity and the rigid internal fixation of plural segments of the spinal column permitting auto-fusion of a given segment. The primary purpose of such surgery is often to prevent worsening of the deformity. A secondary purpose is usually to achieve some correction of the deformity in order to improve the global balance of the spinal column.

A variety of fixation anchors to the bone of the vertebrae can be used, depending on the mechanical need. These include pedicle screws, pedicle hooks, supra-laminar hooks, transverse process hooks, sub-laminar wires and sub-laminar tapes or bands, as well as combinations of various of the foregoing. The use of pedicle screws in conjunction with sub-laminar bands or tapes are often a preferred anchoring system in many practical instances.

Pedicle screws provide useful and efficient fixation points on the spine to permit stabilisation of the vertebrae relative to one another and also to permit a degree of manipulation of the vertebrae when correcting the spinal deformity. The pedicle screw heads (many common types of which are termed "tulip heads", by reason of their physical resemblance to the shape of a tulip flower head) are typically configured to permit direct engagement, along with neighbouring pedicle screw heads affixed to adjacent vertebrae, with an elongate stabilising rod, which provides a rigid construct and permits fusion of the spine in the desired position. Screws can be drawn towards a stabilising rod by translative movement using a reduction device, which engages the screw head and draws the screw to the rod by pulling the screw directly onto the rod, before they are finally secured to each other by a locking screw or nut.

However, the use of pedicle screws comes with some disadvantages, especially in the context of being attached directly to a stabilising rod. One fundamental weakness of screws is that the bone-screw interface can sometimes fail in response to excessive axial pull-out forces. This phenomenon may be commonly encountered in scoliosis surgery in particular, and it may significantly weaken the rigid spinal construct created as a means of treating it. This can sometimes be a particularly significant issue at the concavity of the apex of the scoliotic curve, owing to both the abnormal anatomy of the vertebrae in this region of the spine and also the greater translative distance the spine has to travel in being drawn onto a stabilising rod in this region.

Sub-laminar bands or tapes are better able to resist axial pull-out forces than screws, although they may have a limited ability to transfer torsional forces to the spine and to derotate deformities. Nevertheless, sub-laminar bands or tapes are frequently used to good effect in combination with pedicle screws, and such combinations may even be used in combination with stabilising rods to fulfil additional stabilisation or derotation functions. However, sub-laminar bands or tapes need anchoring to pedicle screws by some means.

There are known in the art devices for attaching sub-laminar bands or tapes to pedicle screw heads. One such known device is known as the "JAZZ Cap" [trade mark] system, from the company Implanet. This device employs a collar-like cap placed over a screw head and from a side of which protrudes a hoop-like extension through and within which a sub-laminar band or tape passes and is clamped, leaving the screw head to be unitable with a stabilising rod in a conventional manner. However, such an anchoring device has limited usefulness in practice, owing to its configuration and reliance on the conventional rod-locking screw/nut to anchor the collar-like cap onto the screw head.

Indeed, the design and function of such known band/tape attachment devices are generally only to provide additional stability once a conventional stabilising rod has been secured to the screw, and deformity correction has been attempted. Their design and function is not to achieve additional deformity correction at the apex of the spinal curve or to increase axial load strength of the apical screws during correction manoeuvres. Furthermore, the anatomy of a scoliotic spine poses special technical difficulties, particularly around the apex of the concavity of the curve, such as:

(i) the pedicles may often be small and mis-shapen, making secure fixation of a pedicle screw more difficult and resulting in reduced pull-out strength;

(ii) the concavity pedicles are crowded together, making sequential placement of screws, and their subsequent attachment to a rod, more difficult;

(iii) the apical pedicle screws are typically furthest from the rod, thus requiring greater translation of the screws towards the rod, which further risks pull-out of screws and loss of fixation;

(iv) reduction devices attached to these screws are often convergent upon one another, making their use technically more difficult and load-sharing in spinal translation sub-optimal.

In view of the above shortcomings in the known art, there is a clinical need for a spinal implant system which has the benefits of a screw in terms of fixation and derotation capability, while maximising pull-out strength to allow superior translation of apical vertebrae towards, and/or rotation of vertebrae relative to, a stabilisation rod during deformity correction manoeuvres.

It is therefore a primary object of the present invention to address the above shortcomings of the known art and, in a major aspect, to provide an anchoring system that facilitates and renders more efficient and effective the anchoring of one or more sub-laminar bands or tapes to, or with respect to, a pedicle screw.

SUMMARY OF THE INVENTION

Accordingly, in a first aspect the present invention provides an anchoring device for anchoring one or more sub-laminar bands or tapes to a pedicle screw, the device comprising:
  a first portion configured for attachment to at least a base portion of a head portion of the pedicle screw; and
  at least one second portion for anchoring thereto a or a respective sub-laminar band or tape;
  wherein the first portion includes first interengagement means for interengagement with the head portion of the pedicle screw to effect the said attachment of the first portion of the anchoring device thereto.

In a second aspect, the present invention provides an anchoring arrangement for anchoring one or more sub-laminar bands or tapes with respect to one or more spinal vertebrae in corrective spinal vertebral surgery, the arrangement comprising:
  a pedicle screw for insertion into a selected vertebral pedicle; and
  an anchoring device for anchoring the or a respective one of the sub-laminar bands or tapes to the pedicle screw, the anchoring device comprising:
    a first portion configured for attachment to at least a base portion of a head portion of the pedicle screw, and
    at least one second portion for anchoring thereto the or the respective sub-laminar band or tape,
    wherein the first portion includes first interengagement means for interengagement with the head portion of the pedicle screw to effect the said attachment of the first portion of the anchoring device thereto.

In some embodiments of the above-defined anchoring arrangement, the head portion of the pedicle screw may comprise second interengagement means configured for interengagement with the first interengagement means provided on the first portion of the anchoring device, whereby the first and second interengagement means are each configured so that they together, once they are interengaged with each other, effect the said attachment of the first portion of the anchoring device to the head portion of the pedicle screw.

Thus, in accordance with a third aspect of the present invention, there is provided a pedicle screw for insertion into a pedicle of a selected spinal vertebra in corrective spinal vertebral surgery, the pedicle screw comprising a head portion which includes second interengagement means configured for interengagement with first interengagement means provided on a first portion of an anchoring device according to the first aspect of the invention or any embodiment thereof.

Moreover, in accordance with a fourth aspect of the present invention, there is provided, as a kit or set of component parts:
  at least one pedicle screw according to the preceding aspect of the invention or any embodiment thereof, together with
  at least one anchoring device according to the first aspect of the invention or any embodiment thereof.

In some embodiments of the above-defined kit or set of component parts, the kit or set may further comprise one or more sub-laminar bands or tapes.

In accordance with a fifth aspect of the present invention, there is provided a method of anchoring one or more sub-laminar bands or tapes with respect to one or more spinal vertebrae in corrective spinal vertebral surgery, the method comprising:
  providing at least one pedicle screw according to the third aspect of the invention or any embodiment thereof, and at least one anchoring device according to the first aspect of the invention or any embodiment thereof;
  inserting the pedicle screw into a pedicle of a selected vertebra;
  attaching the first portion of the anchoring device to at least the base portion of the head portion of the pedicle screw by interengagement of the first and second interengagement means provided respectively on the first portion of the anchoring device and the head portion of the pedicle screw; and
  anchoring the or a respective sub-laminar band or tape to the or a respective second portion of the anchoring device.

In practical embodiments of the above-defined method, the final step of anchoring the or a respective sub-laminar band or tape to the or a respective second portion of the anchoring device may be accompanied or followed by one or more additional steps comprising:
  tightening (e.g. to any extent necessary) the or the respective anchored sub-laminar band or tape in a tightened condition once it has been passed or threaded around at least one vertebra, and
  locking or securing the or the respective anchored sub-laminar band or tape in a tightened condition, especially by means of a suitable locking or securement device (examples of which are well-known in the art).

In embodiments of the various aspects of the invention, the anchoring device may include any of various features, including any of various optional or preferred features, as defined and discussed hereinbelow, independently of any pedicle screw or sub-laminar band or tape or other component of any anchoring arrangement or kit forming other aspects of the invention. Likewise, in embodiments of the various aspects of the invention, the pedicle screw may include any of various features, including any of various optional or preferred features, as defined and discussed hereinbelow, independently of any anchoring device or sub-laminar band or tape or other component of any anchoring arrangement or kit forming other aspects of the invention.

In some embodiments of the anchoring device of the invention, the first portion may be configured for attachment to the head portion of the pedicle screw by interengagement of the first interengagement means with at least an outer sidewall portion, especially a radially outer sidewall portion, of the screw head portion.

In some such embodiments, the first portion may be configured such that, upon interengagement of the first interengagement means with the outer sidewall portion of the screw head portion, at least a lower part of the first portion of the device adjacent the first interengagement means abuts or lies adjacent or engages a lower sidewall portion of the screw head portion.

Thus, in accordance with an alternative first aspect of the invention, there may be provided an anchoring device for anchoring one or more sub-laminar bands or tapes to a pedicle screw, the device comprising:
  a first portion configured for attachment to a head portion of the pedicle screw; and
  at least one second portion for anchoring thereto a or a respective sub-laminar band or tape;

wherein the first portion is configured for attachment to at least a base portion of the head portion of the pedicle screw, and optionally wherein the first portion includes first interengagement means for interengagement with the head portion of the pedicle screw to effect the said attachment of the first portion of the anchoring device thereto.

In some embodiments of the anchoring device of the invention, the first portion of the device may be configured such that it is attachable to the head portion of the pedicle screw, via the interengagement therewith of the first interengagement means, by means of insertion of a screw-threaded shaft of the pedicle screw, which shaft extends from a base of the head portion, through a hole or aperture in the first portion of the device in a direction away from the first portion of the device and relative movement towards one another of the first portion of the device and the base of the screw head portion.

In some embodiments of the anchoring device of the invention, the first portion may comprise a base portion and one or more, especially at least one pair of mutually oppositely arranged, attachment portions extending generally perpendicularly therefrom. The base portion may be apertured or hollow, e.g. with a suitably sized circular or other shaped hole or aperture therein, to allow passage therethrough of the screw-threaded shaft of the pedicle screw during the attachment of the anchoring device thereto.

In some embodiment forms, the attachment portions, which may be configured as a pair of diametrically oppositely arranged protruding lugs, tabs, arms or other engagement elements extending perpendicularly from the base portion on opposite, especially diametrically opposite, sides thereof, may be disposed so as to be generally substantially parallel to one other and configured to interengage with the outer sidewall of the head portion of the screw on opposite, especially diametrically opposite, sides of the screw head portion.

In some such embodiment forms, the attachment portions may each terminate at a distal end thereof (that being the end thereof opposite a proximal end thereof at which the respective attachment portion is joined to the base portion of the first portion of the device) in a radially inwardly projecting interengagement nose portion, whereby the interengagement nose portions of the pair of attachment portions point generally towards one another from opposite sides, especially diametrically opposite sides, of the first portion of the device.

In some such embodiment forms, each interengagement nose portion may include an obliquely inclined interengagement surface therebeneath, especially an obliquely inclined interengagement surface between the respective nose portion and a radially inner side surface of the respective attachment portion to which the respective nose portion is joined, wherein the angle of inclination of each respective interengagement surface is such that a radially inner end of each respective nose portion is closer to the base portion of the first portion of the device than is a radially outer end of the respective nose portion. In other words, in such embodiment forms each interengagement nose portion may comprise a lower interengagement surface, which is that surface directed towards the base portion of the first portion of the device, which forms an angle of less than 90 degrees, e.g. an angle in the range of from about 50 or 60 or 70 to about 80 or 85 or 87 degrees, with a radially inner side surface of the respective attachment portion to which the respective nose portion is joined.

Accordingly, in some such embodiment forms, the respective interengagement nose portions of the pair of attachment portions may form a snap-fit attachment mechanism with the second interengagement means on the head portion of the pedicle screw.

In practising such "snap-fit" embodiments of the anchoring device, for the purpose of bringing the anchoring device and the pedicle screw together and enabling the snap-fit connection between the first and second interengagement means to be made, if desired or necessary a suitable tool may be employed for drawing the two parts together and making the snap-fit attachment connection.

Thus, in some embodiments of the pedicle screw aspect of the invention, the pedicle screw may comprise:

a head portion; and a screw-threaded shaft portion extending from the head portion;

wherein the head portion includes second interengagement means configured for interengagement with the first interengagement means provided on the first portion of the anchoring device, which anchoring device may be an anchoring device according to the first aspect of the invention or any embodiment thereof.

In some embodiments of the pedicle screw of this aspect of the invention the second interengagement means may be provided on, or formed in or on, an outer sidewall portion, especially a radially outer sidewall portion, of the screw head portion. In some embodiments the second interengagement means may comprise one or more, especially at least one pair of oppositely arranged, notches or recesses each for accommodating therein a respective interengagement nose portion of a respective attachment portion extending generally perpendicularly from the base portion of the anchoring device. The pair of notches or recesses of the second interengagement means may be arranged on opposite sides, especially diametrically opposite sides, of the head portion, and facing in opposite radially outward directions from each other.

In some such embodiments each notch or recess of the second interengagement means may include an obliquely inclined interengagement surface therewithin, wherein the angle of inclination of each respective interengagement surface is such that a radially inner end of each respective notch or recess is closer to a lower sidewall portion of the screw head portion than is a radially outer end of the respective notch or recess. In other words, in such embodiment forms each interengagement notch or recess may comprise a lower interengagement surface therewithin, which is that surface directed towards the lower sidewall portion of the screw head portion, which forms an angle of less than 90 degrees, e.g. an angle in the range of from about 50 or 60 or 70 to about 80 or 85 or 87 degrees, with a radially inner side surface of the respective notch or recess.

Thus, in such embodiments the internal shape and configuration of each notch or recess of the second interengagement means, or at least the configuration and orientation of the respective interengagement surfaces of the respective notches or recesses of the second interengagement means, may substantially match (or be complementary to) the outer shape and configuration of the respective interengagement nose portions of the respective attachment portions of the first portion of the anchoring device. In this manner, in such embodiments, the respective notches or recesses of the second interengagement means may form a snap-fit attachment mechanism with the respective interengagement nose portions of the pair of attachment portions.

In practical embodiment forms of the pedicle screw aspect of the invention, the upper part of the screw head portion may be configured in any conventional manner, such as in the form of a discontinuous collar, e.g. with a generally cylindrical or tubular shape (which may be of any suitable cross-sectional shape, e.g. circular, elliptical, generally rectangular, or any other suitable shape), with the collar having the respective notches or recesses of the second interengagement means formed in the respective radially outer sidewall potions thereof.

Alternatively or additionally in such practical embodiment forms of the pedicle screw, the upper part of the screw head portion may be further configured in a conventional manner so as to include a central channel, recess, slot or through-hole therein for accommodating therein a conventional stabilising rod for use in the corrective spinal vertebral surgical operation, and/or to include a screw-threaded locking hole or recess or stub/spigot for having affixed therein or thereto a screw-threaded locking screw or nut for locking such a stabilising rod to the screw head portion—which in either case may only be in embodiments in which such a direct connection between such a screw and such a stabilising rod is desired to be employed.

In order to facilitate the above-mentioned use of a tool for effecting the drawing together of the screw head portion and the anchoring device to form the snap-fit connection therebetween, the upper sidewall part of the screw head portion may be yet further configured to have one or more, especially a pair of, lateral secondary notches or recesses therein, for enabling such a tool to securely grasp the screw head portion in the drawing together of the two parts and the effecting of the snap-fit connection.

In practical embodiments, pedicle screws according to the invention or for use with anchoring devices within the scope of other aspects of the invention, may be made from any suitable material, in particular for example from a surgically acceptable metal or metal alloy. Suitable metal alloys may include various titanium alloys (such as an alloy of titanium with one or more other metallic elements selected from the group consisting of: Al, V, Cr, Mn, Fe, Co, Ni, Cu, Zr, Nb, Mo, Sn, Ta, Pd, Ru), cobalt-chromium (CoCr) alloys, and cobalt-chromium-molybdenum (CoCrMo) alloys Other metal alloys known for use in various surgical implants may also be suitable.

In the anchoring device of the invention, the device comprises at least one second portion for anchoring thereto a or a respective sub-laminar band or tape. In some such embodiments a plurality of second portions may be provided, each being configured and arranged for anchoring thereto a respective one of a plurality of sub-laminar bands or tapes. In some embodiment forms the plurality of second portions may be arranged equi-angularly or symmetrically around (or radially external to) the first portion of the device. The or each such second portion may be integral with the first portion of the device. Furthermore, in some practical example forms the or each such second portion may be formed together with the first portion of the device as a unitary moulding or casting.

In some such embodiments, the device may comprise at least one pair of second portions, which may be symmetrically arranged extending from opposite, especially diametrically opposite, sides of the first portion of the device and extending in radially opposite directions therefrom. The or each second portion may be configured as a hoop or loop, especially one with a generally circular internal shape, or as a land, flange or tab extending from the first portion of the device and with an aperture or through-hole formed therein.

Thus, in accordance with another alternative first aspect of the invention, there may be provided an anchoring device for anchoring one or more sub-laminar bands or tapes to a pedicle screw, the device comprising:
 a first portion configured for attachment to a head portion of the pedicle screw; and
 a plurality of second portions each for anchoring thereto a or a respective sub-laminar band or tape.

In some embodiments of the above-defined alternative anchoring device, the plurality of second portions may be symmetrically arranged equi-angularly around (or radially external to) the first portion of the device, and/or may extend from opposite, especially diametrically opposite, sides of the first portion of the device and extending in radially opposite directions therefrom. In some such embodiments each second portion may be configured and arranged for anchoring thereto a respective one of a plurality of sub-laminar bands or tapes.

In some such embodiments, each of the plurality of second portions of the device may be configured so as to lie in a general plane with is substantially co-planar with the corresponding general plane(s) of the other second portion(s) of the device and/or with a general plane of a base portion of the anchoring device from which extend the respective first interengagement means which provide the attachment to the pedicle screw head portion.

In practical embodiment forms of the anchoring device of the invention, the second portion(s) and the central, first portion may be formed, especially together as a unitary moulding or casting, from any suitable material. Suitable materials may include titanium or a titanium alloy (e.g. an alloy of titanium with one or more other metallic elements selected from the group consisting of: Al, V, Cr, Mn, Fe, Co, Ni, Cu, Zr, Nb, Mo, Sn, Ta, Pd, Ru), various cobalt-based alloys (e.g. alloys of cobalt with chromium and/or molybdenum), as well as various suitably strong and rigid synthetic plastics materials (specific examples of which are already known in the art of synthetic surgical implants).

In general, in practical embodiments, any metal or metallic alloy used to form the anchoring device may desirably be of a material that is chemically compatible with the material from which the associated pedicle screw is formed. By this is meant that the respective materials of the anchoring device and the pedicle screw head portion with which it comes into prolonged contact once in use substantially do not create or lead to any significant mutually-induced corrosion or cold-welding phenomena during their extended use and presence in the spinal cavity of a patient.

In some embodiments of the anchoring device of the invention, the or each second portion may have mounted therein an insert for providing the means of anchoring to that second portion of the device the or the respective sub-laminar band or tape. The or each insert may be manufactured from any suitable plastics material, for example, although other materials (e.g. a metal or metal alloy) may be possible.

In some such embodiments the or each insert may comprise a central body, in which there is provided a slot or aperture through which passes or is accommodated the or the respective sub-laminar band or tape, and an outer frame configured for mounting the insert in the respective second portion of the device. In some such embodiments the outer frame may be configured for being engageable in the respective second portion of the device by means of a snap-fit connection.

In some such embodiments the central body of the or the respective insert may take the form of a short, circular cylinder, which is mounted rotatably, especially freely rotatably, within a geometrically similar circular mounting within the respective frame, so that the orientation of the slot or aperture therein may vary or be self-adjusting so as to adopt an optimum orientation as dictated by the various forces that may be exerted on the anchoring device by the one or more sub-laminar bands or tapes once they have been anchored to the device and tightened into their desired secured (or locked) condition.

In some embodiment forms the slot or aperture within the respective central body of each respective insert may be suitably dimensioned to allow the respective sub-laminar band or tape to pass and slide freely therethrough, in which case it is to be expected that a separate discrete securement or locking device is to be employed elsewhere in the overall arrangement for securing the respective sub-laminar band or tape in its tightened condition once it has been deployed in its desired configuration having been passed or threaded around the relevant vertebra(e) and anchored to the anchoring device.

Alternatively, in other embodiment forms, it may be possible for the or each respective slot or aperture within the respective central body of the respective insert to itself include a suitable securement or locking device which allows the respective sub-laminar band or tape to be secured directly within the respective insert of the device. By way of example, a suitable form of such integrated securement or locking device may comprise a one-way-only clamping mechanism, which allows a band or tape to slidingly pass through the slot or aperture in one direction only, e.g. for tightening purposes, yet to be restrained by gripping and prevented from being drawn back through the slot or aperture in the opposite direction.

For use in or with embodiments of the anchoring device of the invention, any suitable known form(s) of sub-laminar bands or tapes may be used, examples of which are well-known in the art. Such sub-laminar bands or tapes may for instance be formed of a non-elastic poly-filament woven or braided material, e.g. of a suitable synthetic plastics or polymeric material (such as polyester terephthalate, among others).

In some alternative embodiments of the anchoring device of the invention, the construction and configuration of its first and at least one second portions may be somewhat simplified, in particular such that the device is formed as a substantially unitary one-piece structure, especially with no incorporated moving parts, and which may be more readily deployed in combination with a simpler modified form of pedicle screw head or even with one or more known designs of pedicle screw head. Such a simpler design of anchoring device may also be cheaper to manufacture.

Thus, in some alternative embodiments of the anchoring device of the invention, instead of the anchoring device and the head portion of the pedicle screw being attachable and unitable by virtue of a snap-fit connection (such as by use of the above-defined first and second interengagement means and the device being brought together with the pedicle screw head portion from below by virtue of the pedicle screw's threaded shaft being inserted through the hole or aperture in the first portion of the device from thereabove), in some alternative embodiments of the invention in its various aspects the anchoring device and the head portion of the pedicle screw may be attachable and unitable by virtue of a push-fit or friction-fit or mere abutment-fit connection, with the anchoring device being able to be brought together with the pedicle screw head portion from above by virtue of the hole or aperture in the first portion of the device being placeable over the pedicle screw's head portion from thereabove and the two parts united by means of alternatively constructed first and second interengagement means on the respective anchoring device and pedicle screw head portion.

Accordingly, in some alternative embodiments of the anchoring device of the invention, the first portion of the device may be configured such that it is attachable to and unitable with the head portion of the pedicle screw, via the interengagement therewith of the first interengagement means, by means of placement of a hole or aperture in the first portion of the device over the pedicle screw's head portion from thereabove, i.e. from the side thereof opposite to that from which extends the pedicle screw's threaded shaft.

In some such alternative embodiments of the anchoring device, the first portion of the device may still or again be configured for attachment to the head portion of the pedicle screw by interengagement of the device's first interengagement means with at least an outer sidewall portion, especially a radially outer sidewall portion, of the screw head portion, but now the first interengagement means may comprise one or more, especially at least one pair of oppositely or diametrically oppositely arranged, flanged or seating or bearing portions, which may be integral with, or formed as extensions of or by portions of, the first portion of the device.

For use in combination with such an alternative embodiment anchoring device, in an alternative form of pedicle screw (some specific forms of which pedicle screw may be embodiment pedicle screws according to that aspect of the invention), the head portion of the pedicle screw may still or again include second interengagement means which are provided on, or formed in or on, an outer sidewall portion, especially a radially outer sidewall portion, of the screw head portion, but now the second interengagement means may comprise one or more, especially a circumferential or alternatively at least one pair of oppositely or diametrically oppositely arranged, externally extending flanges, lips, steps or lands, or possibly even recesses, recessed lands or indentations or shoulders, formed on or in the outer sidewall of the pedicle screw head portion, with which may engage by simple mechanical abutment or seating or bearing the respective corresponding flanged or seating or bearing portion(s) constituting the first interengagement means of the anchoring device.

Thus, in some alternative embodiments of the pedicle screw aspect of the invention, the pedicle screw may still or again comprise:
 a head portion; and
 a screw-threaded shaft portion extending from the head portion;
 wherein the head portion includes second interengagement means configured for interengagement with the first interengagement means provided on the first portion of the anchoring device, which anchoring device may be an anchoring device according to the first aspect of the invention or any embodiment thereof,
 and wherein the second interengagement means are provided on, or formed in or on, an outer sidewall portion, especially a radially outer sidewall portion, of the screw head portion;
 but now the second interengagement means comprise one or more, especially a circumferential or alternatively at least one pair of oppositely or diametrically oppositely arranged, externally extending flanges, lips, steps or lands, formed on the outer sidewall of the pedicle screw head portion, especially with which may engage by simple mechanical abutment or seating or bearing the or the respective first interengagement means of the anchoring device.

In many practical forms of such alternative embodiments of anchoring device and pedicle screw the respective one or more (especially plurality of) flanged or seating or bearing portions constituting the first interengagement means of the anchoring device and the one or more external flanges, lips, steps or lands, or recesses, recessed lands or indentations or shoulders, constituting the second interengagement means of the pedicle screw head portion, may be shaped, dimensioned and positioned relative to each other such that they substantially match or approximate in configuration or fit together with one another in respective pairs thereof such that they may readily unite with each other in a simple abutment or seating or bearing manner, and thus so that the anchoring device and the pedicle screw head portion may be readily unitable by virtue of a simple mechanical slide-over or push-fit or friction-fit connection.

In some such alternative embodiments of anchoring device the device may be formed as a substantially unitary one-piece structure, e.g. by any suitable moulding technique, optionally with cutting out or drilling of any appropriate holes, apertures, slots or slits that may be required for forming other features of the device.

Such one-piece embodiment forms of anchoring device may, as for other embodiment devices, be formed from any suitable material, such as titanium or a titanium alloy (e.g. an alloy of titanium with one or more other metallic elements selected from the group consisting of: Al, V, Cr, Mn, Fe, Co, Ni, Cu, Zr, Nb, Mo, Sn, Ta, Pd, Ru), various cobalt-based alloys (e.g. alloys of cobalt with chromium and/or molybdenum), or various suitably strong and rigid synthetic plastics materials, e.g. polyether ether ketone "PEEK" or similar material, to name just one example thereof amongst many possible alternatives.

Such one-piece embodiment forms of anchoring device may be substantially flat or planar, or alternatively non-flat or non-planar, in general cross-sectional shape. In the case of non-flat/non-planar forms, the anchoring device may be configured for example with at least one portion thereof curved or bent or concave (or convex) or ramped or stepped with respect to the remainder of the device. Such a curved or bent or ramped or stepped portion may for instance be constituted by one of the flanged or seating or bearing portions constituting the first interengagement means of the device.

In some such alternative embodiments of anchoring device, especially those in which the device is formed as a substantially one-piece structure, the construction and configuration of the one or more second portions (for anchoring a or a respective sub-laminar band or tape) may also be somewhat simplified. Accordingly, instead of distinct hoop(s) or loop(s) forming the second portion(s), optionally with a respective insert mounted in a frame portion thereof and including a slot or aperture through which is passable and securable a respective sub-laminar band or tape, the or each respective second portion of the device may comprise one or more, or a plurality of, holes or apertures or slots or slits formed in and/or extending through the material of the device in the respective second portion thereof.

Such second portion(s) of the device, especially a pair of said second portions, containing the said holes/apertures/slots/slits may be arranged or located to either side of the first portion of the device, and especially in the case of a pair of oppositely or diametrically oppositely arranged flanged or seating or bearing portions forming the first engagement means, respective ones of the pair of said second portions may be arranged or located intermediate of or between respective ones of those flanged or seating or bearing portions forming the first engagement means. The or each respective second portion may comprise any number of (especially one or more of or a plurality of) holes/apertures and/or any number of (especially one or more of or a plurality of) slots or slits in any combination or spatial arrangement or distribution, in order to achieve any desired or appropriate anchoring or securing of the respective band or tape passed therethrough. For example, certain one(s) of any such hole(s)/aperture(s) or slots/slits may more appropriately serve a tightening or tensioning function, whereas certain other one(s) of any such hole(s)/aperture(s) or slots/slits may more appropriately serve a securing or locking function.

If desired or necessary, any final anchoring or securement of a respective sub-laminar band or tape in any suitable one (or more) of such hole(s)/aperture(s) or slots/slits may be effected or facilitated by insertion thereinto of a suitable locking element, such as a locking screw, plug or like insertable clamping or locking element, optionally in combination with a suitable grommet, collar or similar anchoring insert. This feature may also apply to the practical deployment of the first embodiment anchoring device as discussed hereinabove.

In certain ones of such alternative embodiment forms, the defining perimeter(s) of any one or more of such hole(s)/aperture(s) or (especially) slots/slits may be wholly contained within the material of the relevant second portion of the device in which it/they is/are formed. However, in certain other ones of such alternative embodiment forms, the defining perimeter(s) of any one or (especially) two or more of such hole(s)/aperture(s) or (especially) slots/slits may be only partially contained within the material of the relevant second portion of the device in which they are formed, so that the relevant hole(s)/aperture(s) or (especially) slots/slits is/are open and unbounded on at least one side or portion thereof, especially on a radially inner side or portion thereof, thereby creating a (or a respective) tab or tongue inbetween at least one pair thereof. This tab/tongue feature may serve to assist the insertion and threading through the slots/slits of the respective sub-laminar bands or tapes, and/or may also serve as a deformable or displaceable member that forms its own interference fit against an outer sidewall portion of the pedicle screw head once it has been inserted into the central hole/aperture of the device upon uniting of the two components together.

Some practical examples of some useful tightening/tensioning and securing/locking arrangements of bands or tapes passed through various hole(s)/aperture(s) and slots/slits in such second portions of such alternative embodiment devices will be described further hereinbelow in the context of some specifically described practical example embodiments of the invention as illustrated in the accompanying drawings.

Within the scope of this application it is expressly intended that the various aspects, embodiments, examples and alternatives set out in the preceding paragraphs, in the claims and/or in the following description and drawings, and in particular the individual features thereof, may be taken independently or in any combination. Thus, any one or more features referred to or described with reference to one particular embodiment should be construed as being applicable to any or all embodiments, unless expressly stated otherwise or such features are incompatible.

BRIEF DESCRIPTION OF THE DRAWINGS

Various embodiments of the various aspects of the present invention will now be described in detail, by way of non-limiting example only, with reference to the accompanying drawings, in which.

DETAILED DESCRIPTION OF EMBODIMENTS

In the accompanying drawings, any specific dimensions (e.g. in mm or cm) that may be annotated thereon are to be considered to be non-limiting and for purely illustrative example purposes only.

Figure 1:
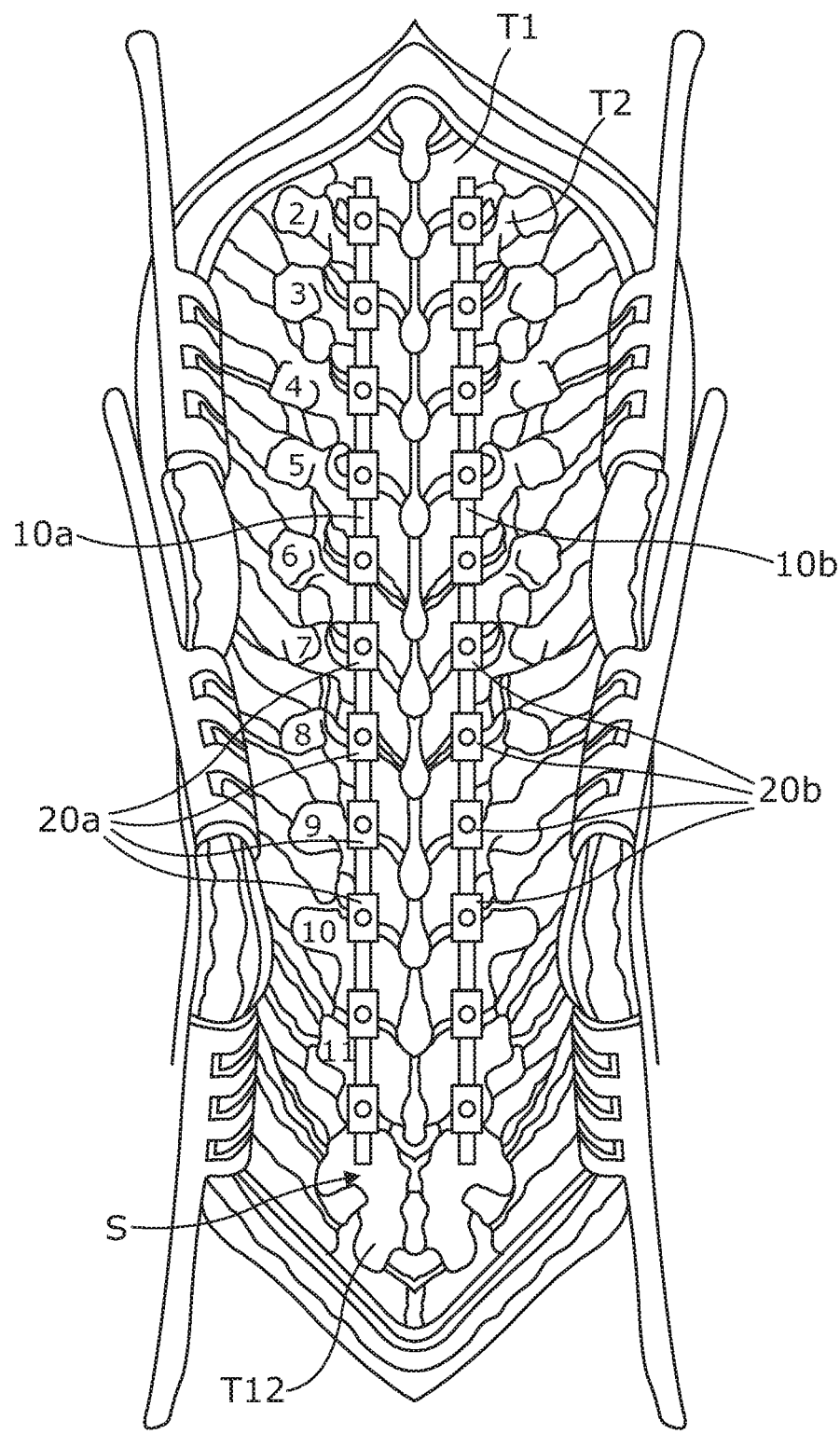
FIG. 1 is an illustrative posterior view of a human spinal region exposed during spinal deformity corrective surgery, showing an example of a pair of rigid constructs formed by a pair of stabilising rods each affixed by a series of screws to the various thoracic vertebrae.
Figure 2:
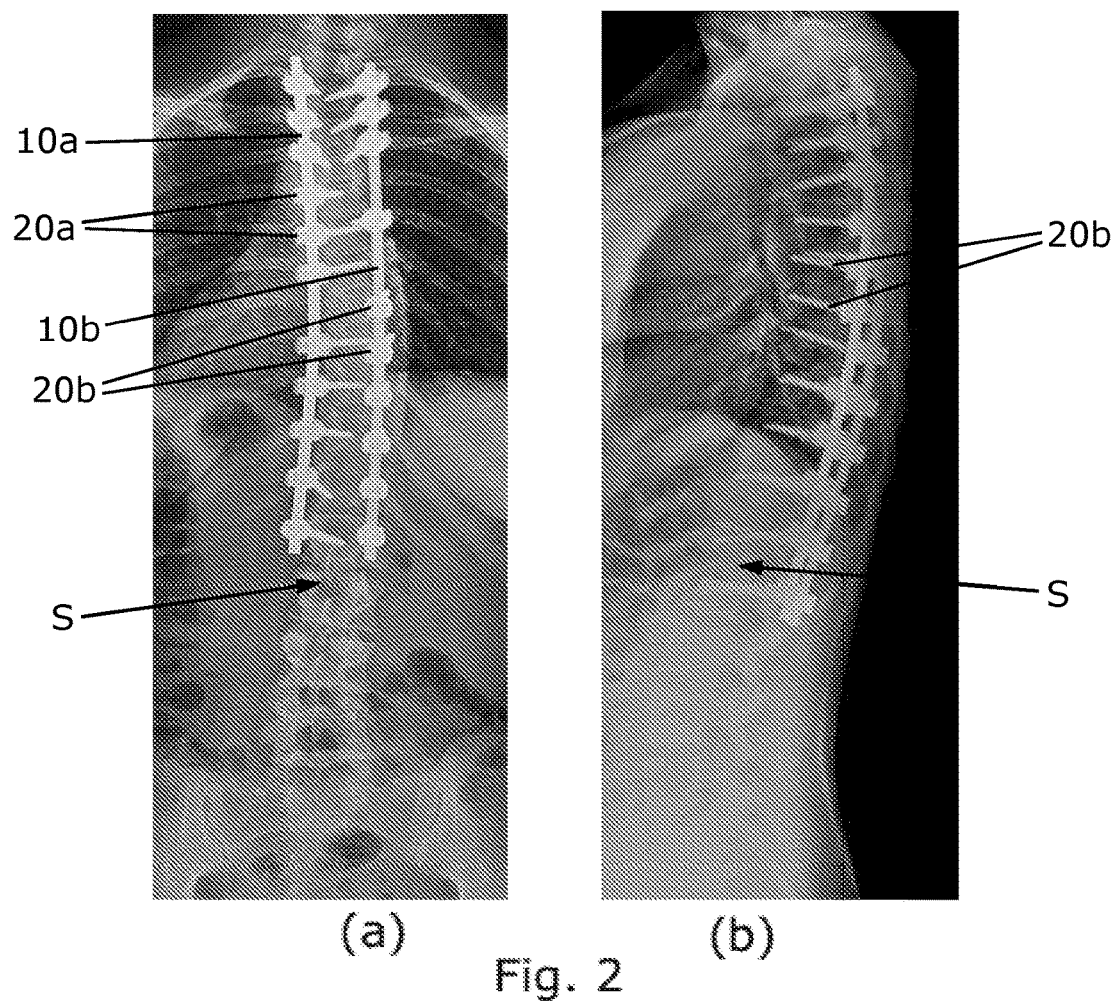
FIGS. 2(a) and (b) are, respectively, a posterior and a left-side x-ray image of the spinal region of FIG. 1, illustrating the typical three-dimensional arrangement of the various screws and rod constructs.

Referring firstly to FIG. 1, this shows purely by way of an illustrative example a human spinal region, in posterior view, which has been exposed during spinal deformity corrective surgery to mount a pair of substantially rigid constructs or assemblies onto the various thoracic vertebrae (labelled conventionally as T1-T12) for the purpose of correcting a spinal deformity such as that caused by scoliosis. In this example, a pair of generally parallel stabilising rods 10a, 10b have been mounted on and secured to a respective series of screws 20a, 20b each of which has been inserted into the bone of a respective pedicle or other part of the relevant vertebra of the spinal column S. FIGS. 2(a) and (b) show the overall spinal implant arrangement more clearly in three dimensions in the form of x-ray images. (It is to be understood, of course, that the arrangement shown in FIGS. 1 and 2 of two elongate stabilising rods 10 and their associated screws being affixed into each of the thoracic vertebrae T1-T12 may well be an extreme example, and it is possible for any shorter or different arrangement of one or any plurality of stabilising rods 10 and any suitable number of attachment/affixation screws 20, e.g. pedicle screws, to be provided for creating any desired size, layout and configurational arrangement for use in anchoring one or more sub-laminar bands or tapes with respective to any one or more of the spinal vertebrae.

In practice, the function of each of the stabilising rods 10*a*, 10*b* of FIG. 1 may typically be supplemented by any suitable number and arrangement of one or more sub-laminar bands or tapes (not shown in FIG. 1), which pass around appropriate portions of the relevant vertebrae and are anchored to the respective rod 10 to provide a means of pulling the spinal column S into the desired corrective configuration and holding it there upon securement or locking of the respective sub-laminar bands or tapes in their tightened state. Typically these steps will be carried out after the final insertion of the screws into the relevant vertebrae pedicles and the accompanying final anchoring and locking (using conventional locking screws/nuts) of the relevant rod onto the heads of the relevant pedicle screws. In this manner the final arrangement enables the necessary corrective relative configuration of each of the relevant vertebrae with respect to the relevant stabilising rod 10 to be assured and maintained. It is generally necessary of course that suitable anchoring points in the arrangement are provided for the relevant sub-laminar bands or tapes so they can exert their corrective torsional and other forces, and these anchoring points can be most usefully provided by the heads of the pedicle screws 20*a*, 20*b* themselves. It is thus to the means of anchoring such sub-laminar bands or tapes with respect to the screws 20*a*, 20*b* that embodiments of the invention in its various aspects are especially directed.

Figure 3:
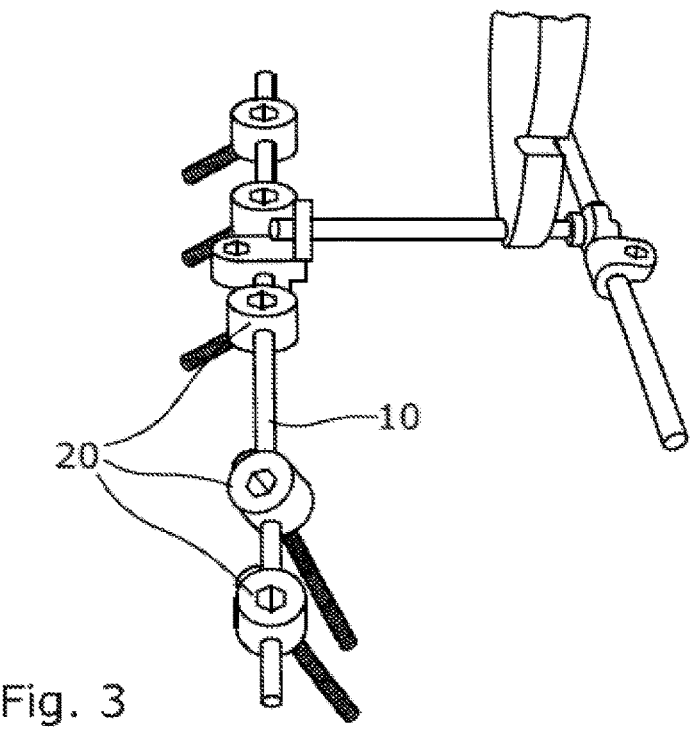
FIG. 3 is a perspective view of another example arrangement, prior to deployment in a patient, of a stabilising rod construct which has had attached thereto, and locked thereon (by locking screws), a series of pedicle screws via their "tulip-heads"

FIG. 3 shows more clearly a representative example of an arrangement, before being deployed in a patient, of a stabilising rod with a series of associated pedicle screws locked thereon (by conventional locking screws) via their "tulip-heads".

Turning now to FIGS. 4 to 7, these various FIGS. show the principal components of an embodiment of an anchoring arrangement useful for anchoring one or more sub-laminar bands or tapes with respect to one or more pedicle screws. The arrangement comprises in particular an anchoring device 40, together with a modified pedicle screw 30 (which is to say a pedicle screw with a modified construction or configuration in comparison with known pedicle screws hitherto known and used in the art), which are unitable together in a novel fashion as a result of their unique and novel constructions. Both the anchoring device 40 and the modified pedicle screw 30 constitute embodiments of independent aspects of the present invention, as is also the overall anchoring arrangement itself.

Figure 4:
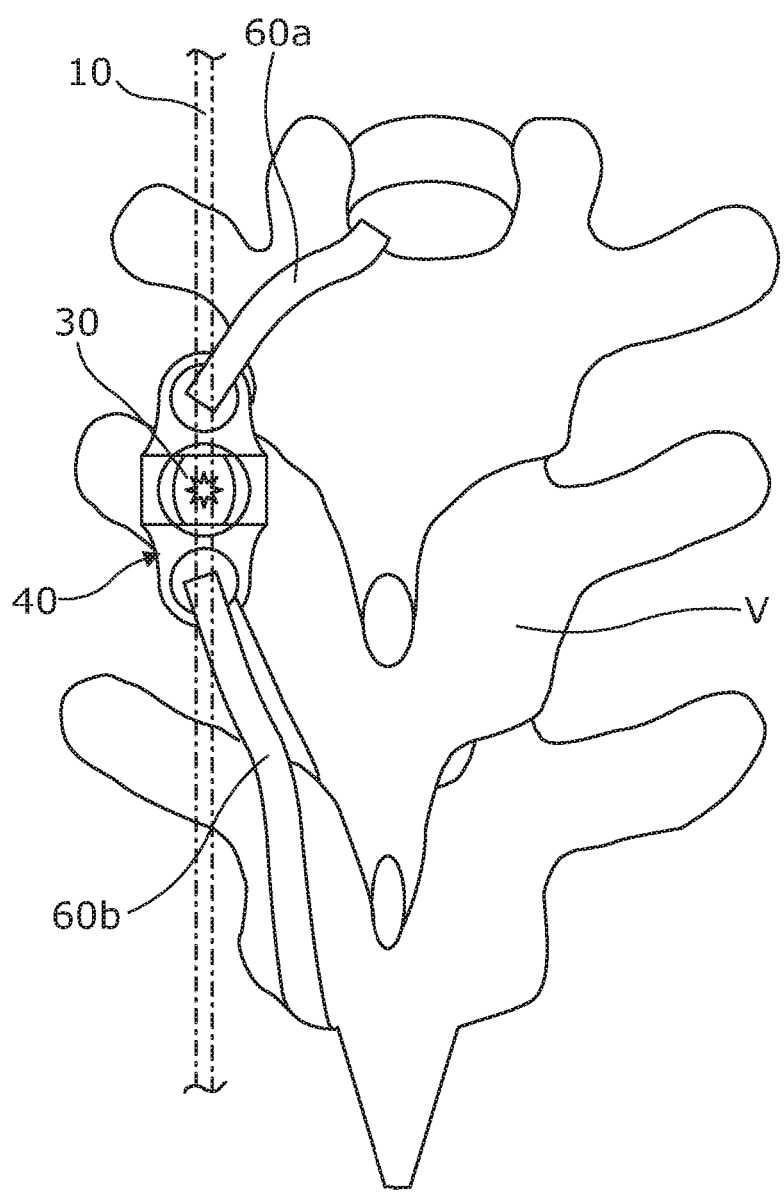
FIG. 4 is a posterior view of an anchoring device according to one embodiment of the present invention, showing the device in situ mounted on a pedicle screw with a pair of sub-laminar bands or tapes anchored to the device, the device ready for uniting with a stabilising rod in a spinal deviation corrective surgical procedure.

As shown in FIG. 4, the anchoring device 40 is shown here in situ having been mounted on the underside or base of (i.e. at least in the region of the lower sidewall portion 32L of) the head portion 32 (see FIG. 5) of a modified pedicle screw 30 with a pair of sub-laminar bands or tapes 60*a*, 60*b* anchored to the device 40, the device 40 being ready for uniting with a stabilising rod 10 (shown in phantom lines for clarity) in a spinal deviation corrective surgical procedure. The sub-laminar bands or tapes 60*a*, 60*b* may be formed of a conventional material, e.g. a non-elastic polyfilament woven or braided material such as of polyester terephthalate or other suitable synthetic plastics or polymeric material. The pedicle screw 30 has been inserted in a known manner into the bone of the pedicle of the relevant vertebra V which is that spinal segment which is to be fixed into a new position in the surgical correction procedure. The anchoring device 40, as well as being securely attached to the head portion 32 of the inserted pedicle screw 30 via their novel respective interengageable features (as described further below), serves as an anchor for anchoring, relative to the screw 30, each of the pair of sub-laminar bands or tapes 60*a*, 60*b*, each of which passes round a respective vertebral lamina of the selected vertebra V, thereby enabling the bands/tapes 60*a*, 60*b* to be used more efficiently and reliably to apply the necessary forces to effect the desired deformity correction.

Indeed, the application of the sub-laminar bands or tapes 60*a*, 60*b* to the adjacent vertebrae above and below the vertebra holding the pedicle screw 30 allows fixation of up to three apical segments with just one effective anchoring arrangement and two bands/tapes. In particular, this novel arrangement may equate to a more efficient use of space, thereby ameliorating the problem of screw-head crowding in the region of the apex of the spinal concavity, which can often present practical difficulties in the deployment of known spinal implants used in known spinal corrective surgical procedures.

Figure 5:
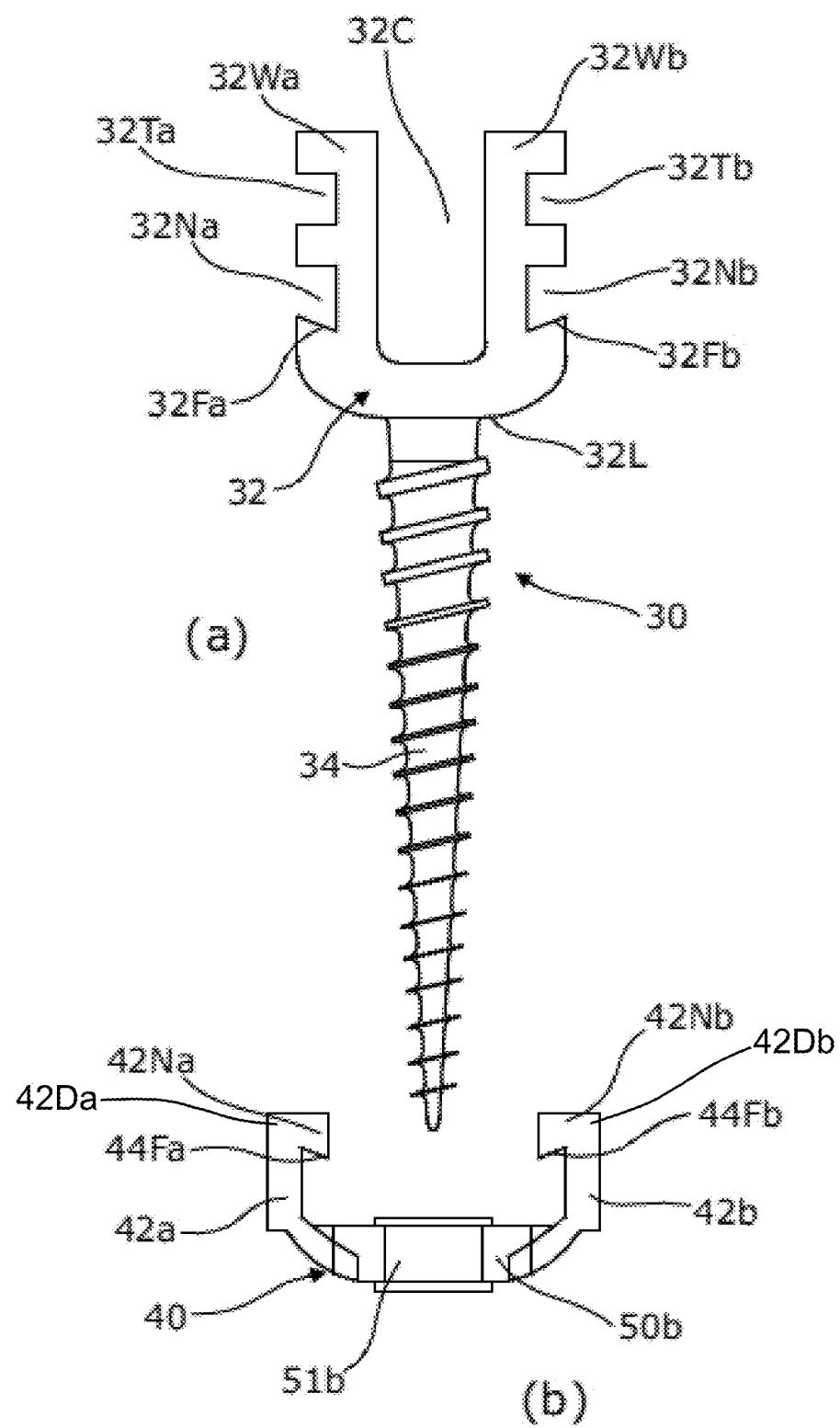
FIGS. 5(a) and (b) are, respectively, a frontal view of a modified pedicle screw and an end-on view of an anchoring device according to embodiments of various aspects of the present invention, for use together in forming an anchoring arrangement of another aspect of the invention.

FIGS. 5(*a*) and 6(*a*) & 6(*b*) show the construction and configuration of one modified pedicle screw 30 in accordance with an embodiment of one aspect of the present invention. The screw, e.g. formed of a conventional titanium alloy, comprises a lower shaft portion 34, which is formed with a conventional screw-thread for insertion (optionally in a pre-drilled hole in the bone) into a selected pedicle or other portion of a selected vertebra, and an upper head portion 32 which is configured to fulfil a dual role—namely to provide a means of attachment to a stabilising rod 10 as well as to provide a site of anchoring for one or more sub-laminar bands or tapes 60*a*, 60*b*. The head portion 32 is formed with an internal channel 32C therein which is sized and configured to accommodate therein a stabilising rod 10, which rod 10 may be locked in the channel 32C in a conventional manner as or when desired by insertion therein of a known form of locking screw (the internal sidewalls of the channel 32C are shown in FIG. 5 as being without any internally screw-thread, for the sake of clarity, although it is to be understood that any suitable internal screw-threading may be employed for this rod-locking purpose. Owing to the configuration of the internal channel 32C, the remnant sidewall portions of the screw head portion 32 may be thought of as being constituted by a pair of diametrically opposed upstanding wall portions 32Wa, 32Wb.

The head portion 32 of the screw 30 is provided on each respective outer sidewall of each of the upstanding wall portions 32Wa, 32Wb with a respective interengagement notch or recess 32Na, 32Nb, each of which is configured to interengage with a respective interengagement detent provided on the first portion of the anchoring device 40 (as described further below). Each interengagement notch or recess 32Na, 32Nb is formed with an obliquely inclined floor surface 32Fa, 32Fb. The angle of inclination of each respective floor surface 32Fa, 32Fb—which may typically be less than 90 degrees, e.g. an angle in the range of from about 50 or 60 or 70 up to about 80 or 85 or 87 degrees, relative to a radially inner side surface of the respective notch or recess 32Na, 32Nb—is therefore such that a radially inner end of each respective notch or recess 32Na, 32Nb is closer to a lower sidewall portion 32L of the screw head portion 32 than is a radially outer end of the respective notch or recess 32Na, 32Nb. Thus, this shape of the lower (i.e. floor) region of each notch or recess 32Na, 32Nb enables it to more assuredly and securely retain therein a respective interengagement detent 42a, 42b (FIG. 7(a)) provided on the central portion of the anchoring device 40 once it has been interengaged therewith.

In order to facilitate the use of a conventional reduction device or other tool for effecting the drawing together of the screw head portion 32 and the anchoring device 40 to form the snap-fit connection therebetween, the upper sidewall part of the screw head portion 32 is further provided with a pair of lateral, straight-walled secondary notches or recesses 32Ta, 32Tb therein, for enabling such a device/tool to securely grasp the screw head portion 32 in the drawing together of the two parts and the effecting of the snap-fit connection.

FIGS. 5(b) and 7(a), 7(b), 7(c) & 7(d) show the construction and configuration of the anchoring device 40 which is in accordance with an embodiment of a primary aspect of the present invention. The anchoring device 40 comprises a central first portion 41, which includes a lower generally cylindrical or annular or toroidal base portion thereof which, once the anchoring device 40 has been interengaged with the screw head portion 32 by means of the respective first and second interengagement snap-fit features (as described further below), substantially abuts the lower sidewall portion 32L of the screw head portion 32. The base portion is apertured or hollow, e.g. with a suitably sized circular hole or aperture 48 therein for allowing passage (in a relatively downward direction, as shown in the drawing) therethrough of the screw-threaded shaft 34 of the pedicle screw 30 during the attachment (in a relatively upward direction, as shown in the drawing) of the anchoring device 40 thereto.

Extending or protruding upwardly from, and especially perpendicularly upwardly from, opposite sides of the base portion of the central portion 41 of the device 40 are a pair of mutually facing attachment portions 42a, 42b, which take the form of a pair of diametrically oppositely arranged, and generally mutually parallel, protruding lugs, tabs or arms 42a, 42b. Each attachment portion 42a, 42b terminates at a distal end 42Da, 42Db thereof in a respective radially inwardly projecting interengagement nose portion 42Na, 42Nb, whereby the interengagement nose portions 42Na, 42Nb point generally towards one another from diametrically opposite sides of the central portion 41 of the device 40.

Each interengagement nose portion 42Na, 42Nb includes an obliquely inclined interengagement floor surface 42Fa, 44Fb therebeneath, the angle of inclination of each of which substantially matches (or is complementary to) the corresponding angle of inclination of the respective one of the floor surfaces 32Fa, 32Fb of the notches or recesses 32Na, 32Nb in the outer sidewall of the head portion 32 of the screw 30. The pair of interengagement nose portions 42Na, 42Nb on the anchoring device 40 are thus configured for interengagement with the respective notches or recesses 32Na, 32Nb in the outer sidewall of the screw head portion 32 via the abutting and mating together of the respective pairs of interengaging floor surfaces 32Fa, 42Fa and 32Fb, 44Fb on the two components 32, 40, once they have been brought together into their mutually attached relationship through the resulting "snap-fit" mechanism.

For the purpose of bringing the anchoring device 40 and the pedicle screw 30 together and enabling the snap-fit connection between the respective pairs of interengagement nose portions and notches or recesses 42Na, 32Na and 42Nb, 32Nb to be made, if desired or necessary a suitable tool may be employed for drawing the two components together and making the snap-fit attachment connection. A conventional reduction tool or any other suitable tool or implement may be used for this purpose, for example.

For the purpose of anchoring the one or more sub-laminar bands or tapes 60a, 60b to the anchoring device 40, a pair of generally circular aperture hoop- or loop-like extensions 46a, 46b, e.g. in the form of apertured lands, flanges or tabs, are provided, which extend general radially outwardly from the central portion 41 of the device and may be formed integrally therewith. The pair of apertured extensions 46a, 46b are arranged equi-angularly around, i.e. diametrically opposite one another on opposite sides of, the central portion 41 of the device 40, and they lie generally in the same plane as the general plane of the central portion 41.

The main elements of the anchoring device 40, which is to say at least the pair of apertured extensions 46a, 46b, the central portion 41 and the attachment portions 42a, 42b, are formed together as a unitary moulding or casting, e.g. of a titanium alloy or a suitably strong and rigid synthetic plastic material. In general, however, the material of the anchoring device 40 should be one which is chemically compatible with the material from which the associated pedicle screw 30 is formed, so that the respective materials from which these components are made do not, once they come into prolonged contact with other over time, do not create or lead to any significant mutually-induced corrosion or cold-welding phenomena during their extended use and presence in the spinal cavity of a patient.

As show in FIGS. 7(a), 7(b), 7(c), 7(d) and 8(a) & (b), each of the apertured extensions 46a, 46b has mounted within it a respective insert 50a, 50b, e.g. made from a suitable synthetic plastics material, which inserts 50a, 50b provide the necessary anchoring locations for the anchoring to the device 40 of the respective sub-laminar bands or tapes 60a, 60b.

Each insert 50a, 50b comprises a central body 51a, 51b (e.g. in the form of a short, circular cylinder) in which there is provided an axially-extending slot or aperture 49a, 49b through which is able to be passed or accommodated the respective sub-laminar band or tape 60a, 60b. Each central body 51a, 51b is mounted in a respective outer frame member (e.g. comprising a pair of upper and lower annular plates which carry the central body 51a, 51b therebetween) which is itself mounted in the respective apertured extension 46a, 46b. Each outer frame member of each respective insert 50a, 50b is mounted in the respective apertured extension 46a, 46b by means of a snap-fit connection.

The central body 51a, 51b of each insert 50a, 50b is mounted in its respective frame member in such a way that it is freely rotatable within its frame member so that the orientation of the respective slot or aperture 49a, 49b therein may be variably self-adjusting so as to adopt an optimum orientation as dictated by the various forces that may be exerted on the respective insert 50a, 50b (and the anchoring device 40 generally) by the one or more sub-laminar bands or tapes 60a, 60b once they have been anchored to the device 40 and tightened into their desired secured (or locked) condition.

Figure 8:
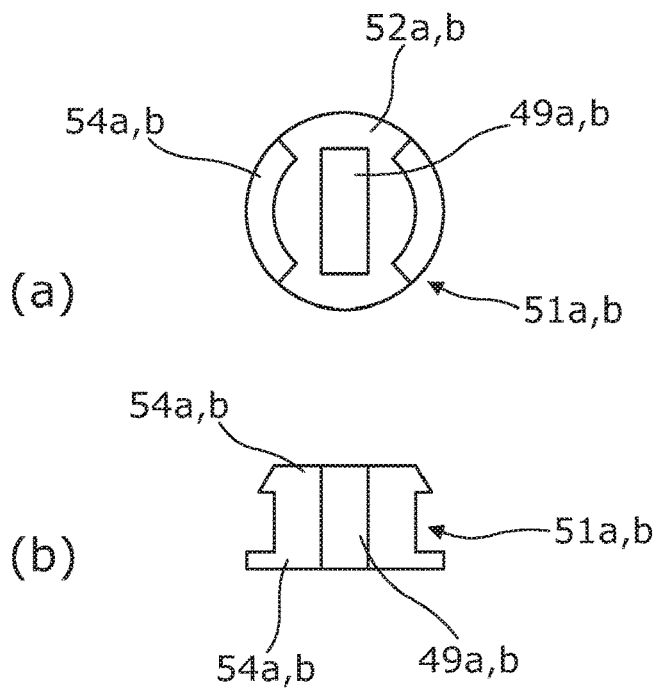
FIGS. 8(a) and (b) are, respectively, a top plan view and side-on view of a central body of an insert for insertion into each of the hoop-like second portions of the anchoring device of FIGS. 7(a)-7(d)

As show in FIGS. 8(a) &(b), each central body 51a, 51b of each insert 50a, 50b is formed as a short, circular cylinder, and comprises a respective solid circumferential rim 52a, 52b on one surface thereof and an incomplete circumferential ring 54a, 54b on the opposite surface thereof, in order to permit a secure placement (e.g. in the manner of a bayonet-type fixing) of the respective central body 51a, 51b in its respective frame member.

In the embodiment shown in the FIGS., each of the slots or apertures 49a, 49b within the respective central bodies 51*a*, 51*b* of the inserts 50*a*, 50*b* is dimensioned to allow the respective sub-laminar band or tape 60*a*, 60*b* to pass and slide freely therethrough, in order to optimise the tightening and final positioning capability of the anchoring device 40. However, in this case it will then generally be required that a separate discrete securement or locking device (not shown) is employed elsewhere in the overall arrangement for securing the respective sub-laminar bands or tapes 60*a*, 60*b* in their tightened conditions once they have been deployed in their desired configurations having been passed or threaded around the relevant vertebra(e) and anchored to the anchoring device 40. Any conventional form of securement or locking device, examples of which are widely used available in the art, may be used for this purpose.

Alternatively, in other embodiment forms, it may be possible for the or each respective slot or aperture 49*a*, 49*b* within the respective central body 51*a*, 51*b* of the respective insert 50*a*, 50*b* to itself include a suitable securement or locking device which allows the respective sub-laminar band or tape 60*a*, 60*b* to be secured directly within the respective insert 50*a*, 50*b* of the device 40. Again, practical examples of suitable such one-way-only clamping mechanisms, which allows a band or tape 60*a*, 60*b* to slidingly pass through the slot or aperture 49*a*, 49*b* in one direction only, e.g. for tightening purposes, yet to be restrained by gripping and prevented from being drawn back through the slot or aperture 49*a*, 49*b* in the opposite direction, are well-known and available in the art.

Looked at in more general terms, the anchoring arrangement of the illustrated embodiment of the invention— especially as it is illustrated in FIG. 4—increases the pull-out strength of the screw 30 by sharing the load exerted by the sub-laminar bands or tapes 60*a*, 60*b* over three spinal segments, allowing greater translational forces to be applied during the deformity correction, as well as a degree of direct vertebral de-rotation at the spinal apex.

Furthermore, using this configuration of anchoring arrangement, the head portion 32 of the screw 30 may still be manipulated and translated towards a stabilising rod 10 if desired or appropriate, and it may also if desired be used to de-rotate the vertebra using conventional reduction tools (examples of which are well-known in the art).

In the formation of the arrangement during a surgical procedure, once the screw 30 is positioned and the bands/tapes 60*a*, 60*b* secured, the screw 30 can then be translated to the rod 10, benefiting from superior pull-out strength, the ability to derotate and potentially to control up to three apical vertebrae with one screw 30, thereby ameliorating the problem of screw-head crowding in the apex of the spinal concavity.

The pedicle screw 30 has been modified, in comparison with a conventional screw, in such a way that the screw "tulip head" 32 can receive the anchoring device 40 which permits the attachments of the sub-laminar bands 60*a*, 60*b*, etc to the screw 30. The device 40 is applied to the base of the screw head 32, in a similar manner to a washer, and is self-secured thereon by a snap-on mechanism. Once the anchoring device 40 is attached, and the bands/tapes 60*a*, 60*b*, etc have been secured to the device 40 and the relevant vertebrae, the screw 30 may then be manipulated directly to the rod 10, allowing translation and de-rotation of up to three segments of the spine per screw 30 onto the rod 10 using a reduction tool that is attached to the tulip head 32.

The sub-laminar bands/tapes 60*a*, 60*b*, etc are positioned under the chosen laminae and looped into the anchoring hoops/loops 46*a*, 46*b* of the anchoring device 40. The pedicle screw tulip head 32 has been modified with a novel pair of notches 32Na, 32Nb at the base 32L of the head 32. These notches 32Na, 32Nb permit the afore-mentioned snap-on attachment of the device 40 to the screw head 32. The device 40 is locked on using a reduction tool that stabilizes the tulip head 32 (via the upper manipulation notches 32Ta, 32Tb) and draws the device 40 onto the screw head 32 until an audible "snap-on" is heard.

Accordingly, by way of practical example only, a summary of the sequence of principal steps used in the deployment of the particular embodiment anchoring arrangement described above may be as follows:

1. The pedicle screw hole is prepared to receive a screw in a standard fashion.
2. Sub-laminar bands 60*a*, 60*b* are positioned beneath the chosen laminae, usually those above and below the level of the screw 30.
3. The bands 60*a*, 60*b* are looped through the anchoring device 40, which can receive two bands 60*a*, 60*b*. Redundant lengths of the bands may be maintained.
4. The device 40 is placed over the shaft 34 of the screw 30 before the screw is advanced into the pedicle.
5. Once the screw 30 is situated, the device 40 is definitively reduced onto the pedicle screw head 32 using a reduction device/tool.
6. The bands 60*a*, 60*b* are then tensioned between the bone and the device 40 and secured/locked in place.
7. The rod reduction tool is then used to translate the screw head 32 (and spine with it) to the rod 10.
8. De-rotation of the spine may then be attempted.
9. A locking screw is then tightened onto the screw head 32, thereby securing the rod 10 thereto.

Although one particular embodiment anchoring arrangement has been described above, and illustrated in the drawings referred to, in terms of an anchoring arrangement which comprises a single anchoring device 40+pedicle screw 30 combination, together with a pair of sub-laminar bands or tapes 60*a*, 60*b*, it is to be understood that other anchoring arrangements also within the scope of the invention may be devised which include any desired or appropriate other numbers of anchoring device+pedicle screw combinations in conjunction with any desired or appropriate number(s) of associated sub-laminar bands or tapes.

Turning now to FIGS. 9 to 18, these FIGS. illustrate an alternative embodiment form of anchoring device 140 within the scope of the invention, which may be used in combination with either an alternative embodiment of modified pedicle screw 130 also within the scope of that aspect of the invention or alternatively still in combination with a known design of pedicle screw 230.

Figures 9A, 9B:
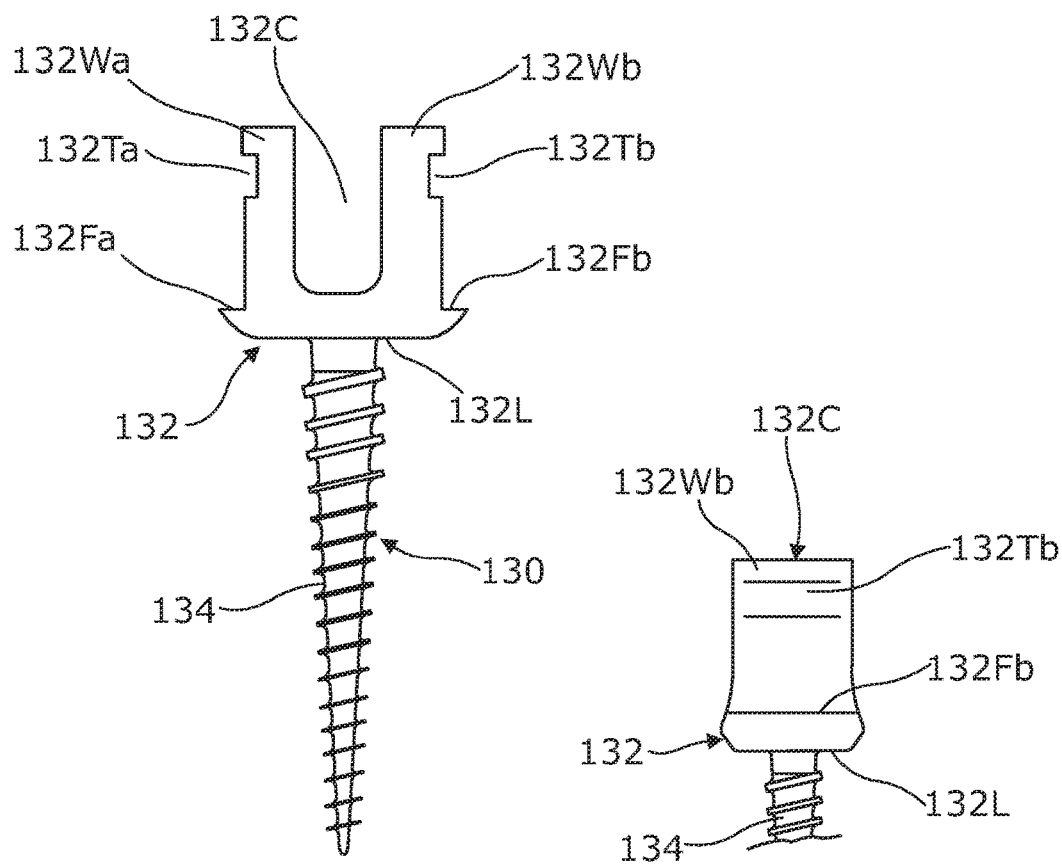
FIG. 9(a) is a frontal view of an alternative form of modified pedicle screw for use with an alternative embodiment of anchoring device according to the invention, in which a push-fit rather than a snap-fit attachment mechanism is employed to unite the two components together.
FIG. 9(b) is a side-on view of the head portion of the alternative modified pedicle screw of FIG. 9(a)
Figure 10:
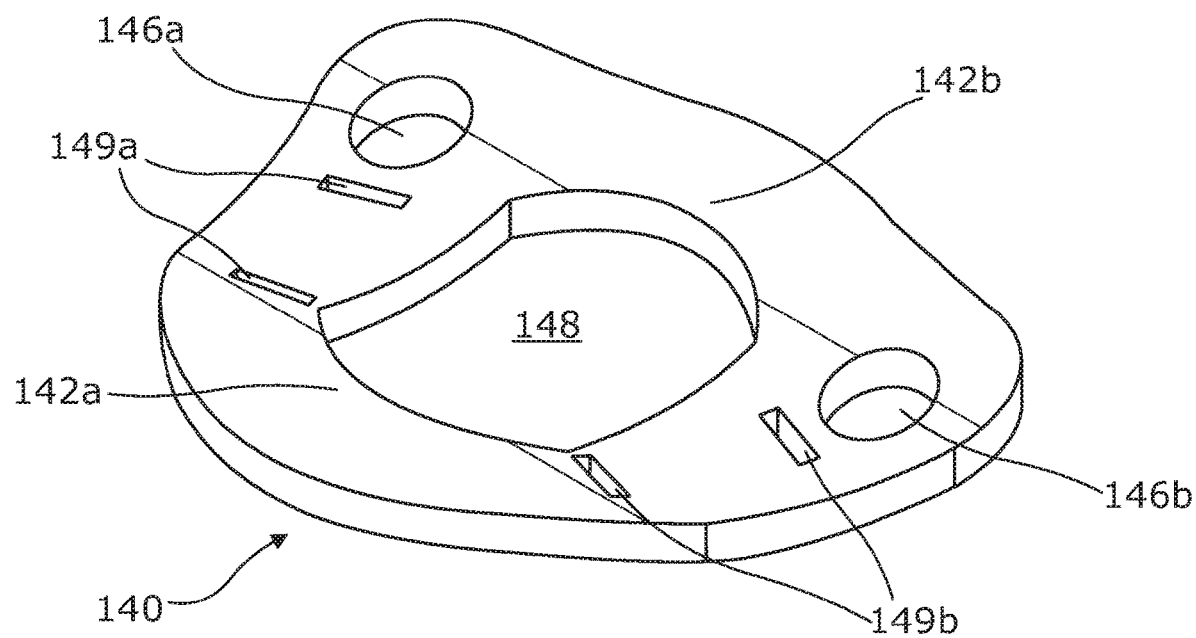
FIG. 10 is a perspective view of an alternative embodiment of anchoring device according to the invention, which is usable in combination with various designs of pedicle screw, including the modified design thereof shown in FIGS. 9(a) & 9(b) but also other known designs such as that shown in FIGS. 12(a) & (b)
Figure 11:
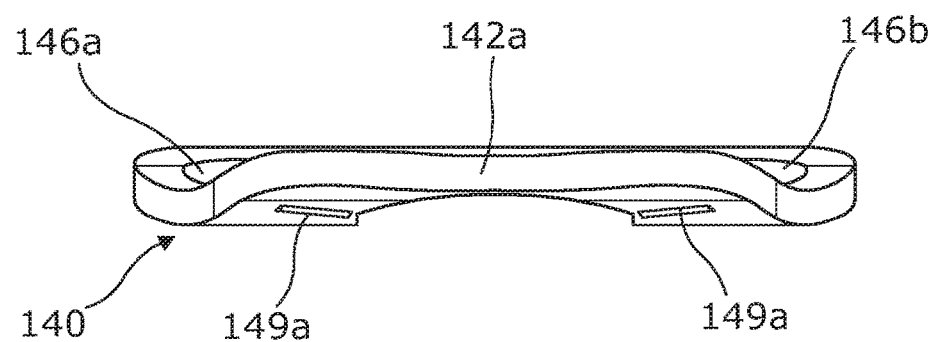
FIG. 11 is a front elevational view of the alternative embodiment anchoring device of FIG. 10.

FIGS. 9(*a*) and 9(*b*) illustrate an alternative form of modified pedicle screw 130 for use with an alternative embodiment form of anchoring device 140 as shown in FIGS. 10 and 11. These two components 130, 140 are unitable together by means of a mechanically simpler push-fit abutment-type connection, rather than a snap-fit attachment mechanism relying on interengaging teeth-like features as in the first embodiment components described above in relation to FIGS. 5 to 7.

As shown in FIGS. 10 and 11, the alternative form of anchoring device 140 is formed as a unitary one-piece structure, e.g. moulded from a titanium alloy or alternatively a suitable polymer material, such as PEEK (polyether ether ketone) or similar. The first, main body portion of the device 140 comprises a central hole or aperture 148 which is placeable over the head portion 132 of the pedicle screw 130

(see FIGS. 9(a) & 9(b)) from thereabove, i.e. from the side thereof opposite to that from which extends the pedicle screw's threaded shaft 134.

The anchoring device 140 includes a pair of oppositely arranged flanged or seating or bearing portions 142a, 142b, each of which is integral with the first, main body portion of the device 140 defining the central hole/aperture 148. The inner perimeter of the central hole/aperture 148 is sized and shaped to substantially match the outer periphery of the head portion (132 in the case of the pedicle screw of FIG. 9, or 232 in the case of the pedicle screw of FIG. 12) of the relevant pedicle screw over which the device 140 is to be fitted.

The first flanged or seating or bearing portion 142a is configured so as to be bent or curved or ramped upwardly relative to the first, main body portion, with the second flanged or seating or bearing portion 142b optionally also being slightly (e.g. to a lesser extent) curved or bent or ramped in either the same or the opposite direction relative to the first, main body portion of the device 140.

Figure 15:
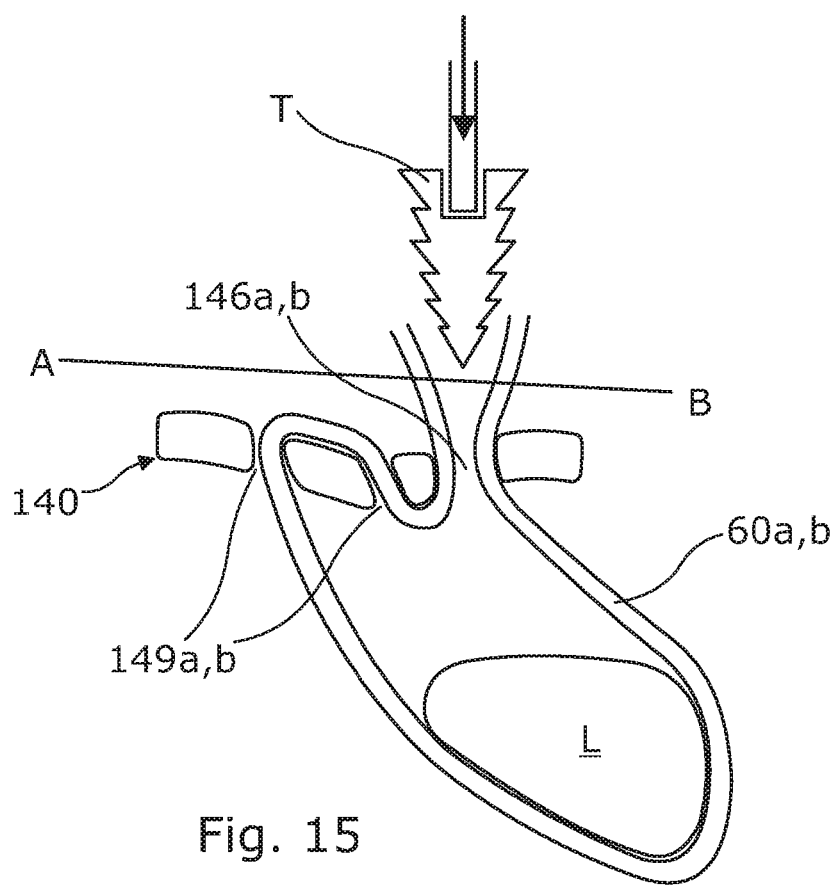
FIG. 15 is a simplified schematic illustration showing one example manner in which a sub-laminar band or tape can be passed through the various apertures and slots./slits of the anchoring device arrangement of FIG. 14 and secured in place therein in order to anchor the band or tape with respect to a spinal vertebral lamina during corrective spinal vertebral surgery.
Figure 17:
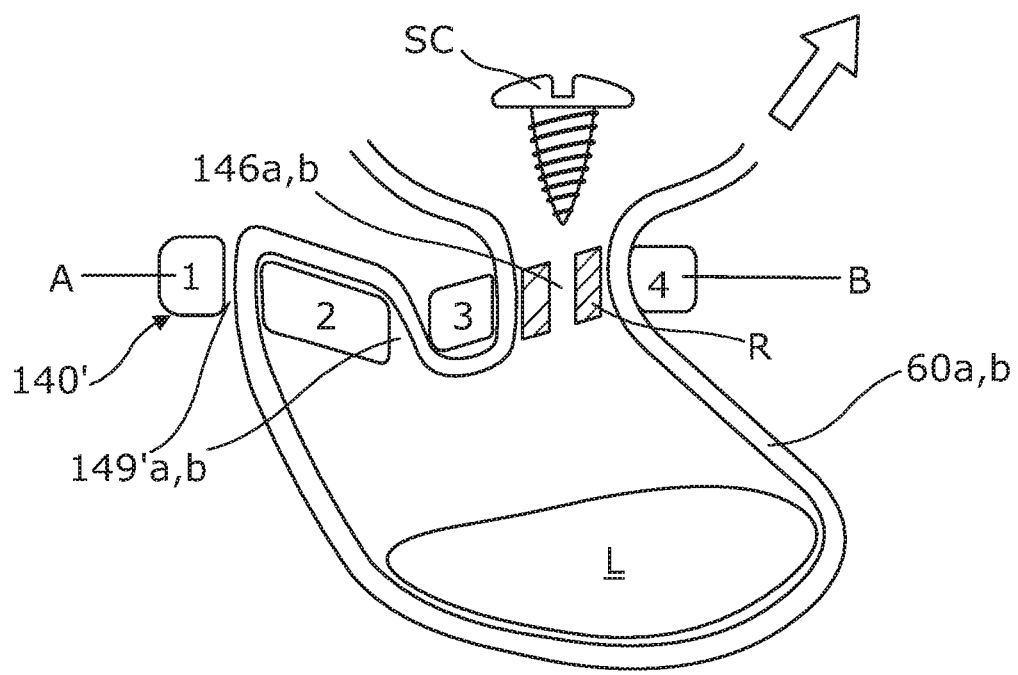
FIG. 17 is a simplified schematic illustration of another example manner in which a sub-laminar band or tape can be passed through the various apertures of the anchoring device arrangement of FIG. 14 or 16 and secured in place therein in order to anchor the band or tape with respect to a spinal vertebral lamina during corrective spinal vertebral surgery.
Figure 18:
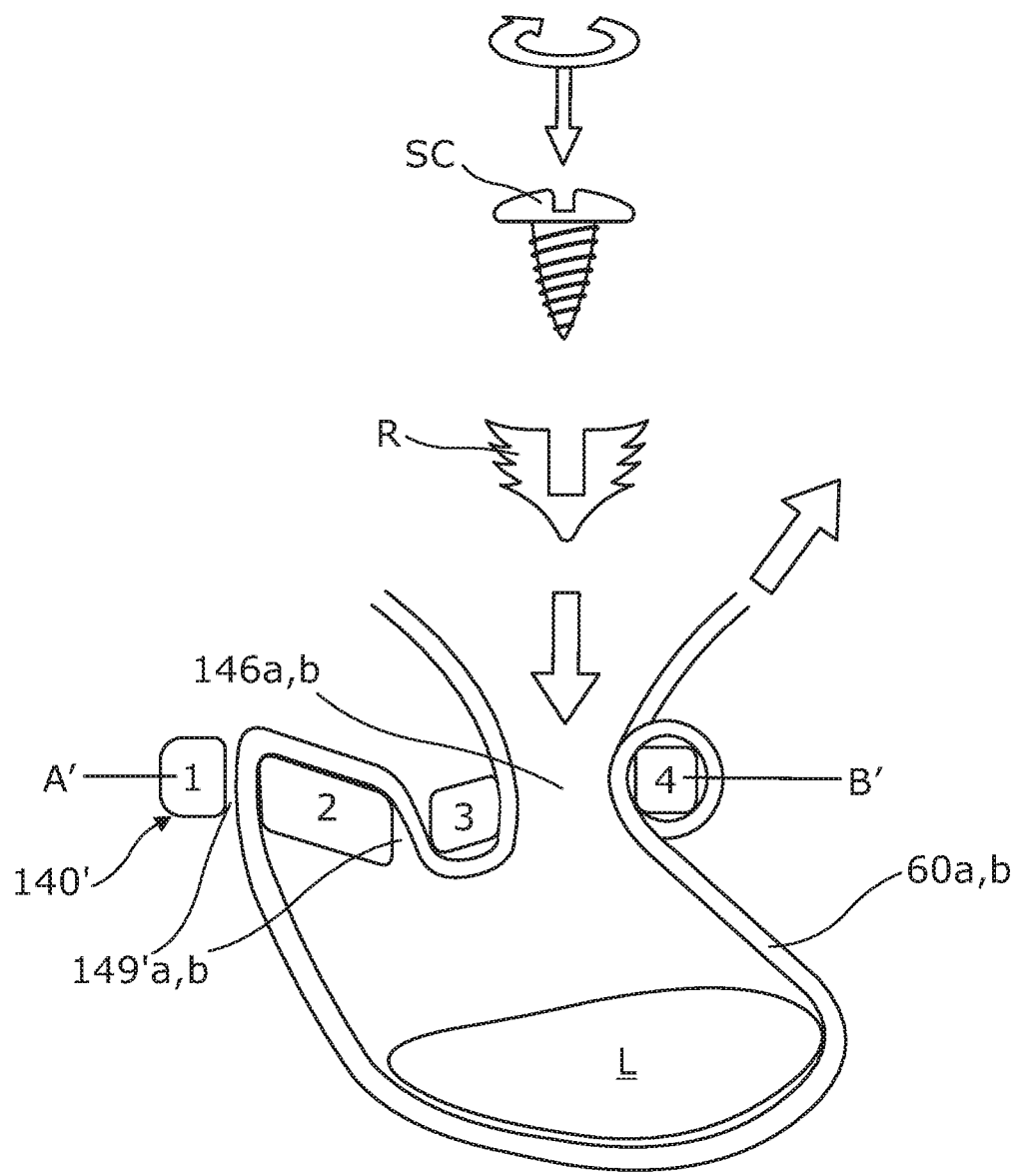
FIG. 18 is a simplified schematic illustration of yet another example manner in which a sub-laminar band or tape can be passed through the various apertures of the anchoring device arrangement of FIG. 14 or 16 and secured in place therein in order to anchor the band or tape with respect to a spinal vertebral lamina during corrective spinal vertebral surgery.

For the purpose of anchoring and securing to the device 140 the relevant sub-laminar band(s) or tape(s) 60a, 60b, the construction and configuration of the second portions of the device are also simplified. As shown in FIGS. 10 and 11, instead of the distinct hoop- or loop-like second portions 46a, 46b together with their respective slot-containing inserts 50a, 50b mounted therein forming the means by which the relevant sub-laminar band(s) or tape(s) 60a, 60b are anchored and secured to the device as in the first embodiments described above, in this mechanically simpler arrangement of this embodiment each respective opposed second portion of the anchoring device 140, to either side of the central hole/aperture 148, is formed with a circular or rounded hole or aperture 146a, 146b extending through the material thereof, and adjacent thereto is further provided a pair of side-by-side but slightly spaced apart (e.g. a few, such as from about 2 or 3 to about 10 mm) and approx. parallel elongated slots or slits 149a, 149b (also extending through the material thereof) for having the relevant respective ones of the sub-laminar bands or tapes 60a, 60b passed therethrough, tensioned or tightened as necessary, and finally secured in place relative thereto. Such final securing may be effected or aided by means of a suitable respective locking screw, plug or like insertable locking or clamping element (e.g. T or SC, as shown in FIGS. 15, 17 & 18), optionally in combination with a suitable grommet, collar or similar insert (e.g. R in FIG. 18), which locking or clamping element T, SC is most usefully insertable into the relevant circular/rounded hole or aperture 146a, 146b.

Figure 14:
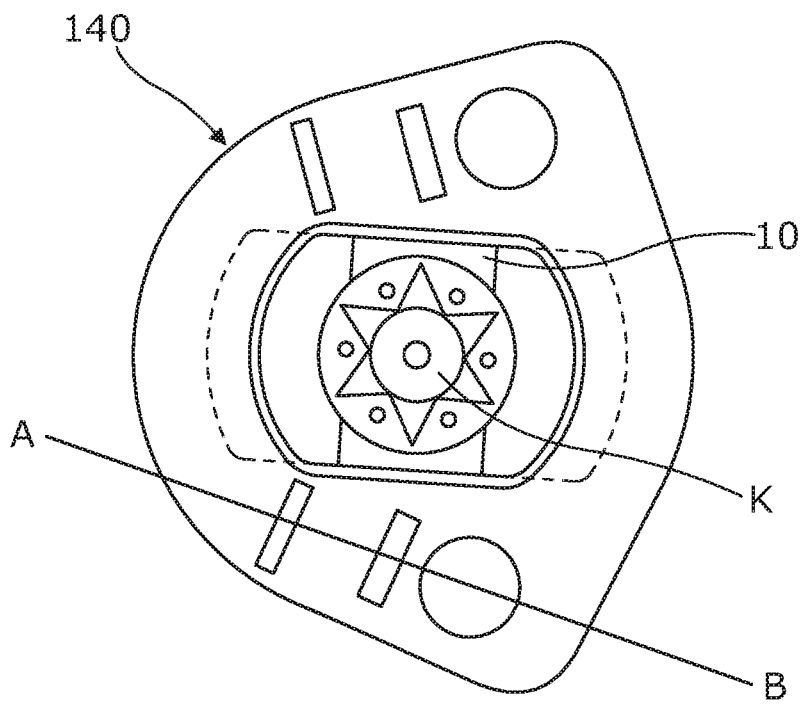
FIG. 14 is a top plan view of the attached combination of FIG. 13, together with a locking screw anchoring a stabilising rod extending through the pedicle screw head, showing the combination ready for receiving various sub-laminar bands or tapes passing through the various apertures and/or slots/slits thereof.

As shown in the embodiment device 140 of FIGS. 10 & 11, the defining perimeters of each of the circular/rounded holes/apertures 146a, 146b and also the defining perimeters of the various anchoring/securing slots or slits 149a, 149b are all wholly contained within the material of the device 140 in which they are formed, as also seen in FIG. 14. However, in certain other alternative embodiment forms of device 140' such as that shown in FIG. 16, the defining perimeters of the various anchoring/securing slots or slits 149'a, 149'b are only partially contained within the material of the device 140' in which they are formed, so that each respective slot/slit 149'a, 149'b is open and unbounded on one short side, i.e. a radially inner side, thereof. This alternative configuration of such slots/slits 149'a, 149'b as in FIG. 16 serves to create a respective tab or tongue 151'a, 151'b between each respective pair thereof. Each tab or tongue 151'a, 151'b may facilitate the overall insertion and threading through the slots/slits 149'a, 149'b of the respective sub-laminar bands or tapes 60a, 60b and/or may also serve as a deformable or displaceable member that forms its own interference fit against the outer sidewall of the pedicle screw head portion once it has been inserted in to the central hole/aperture of the device 140'.

For use in combination with the alternative embodiment form of anchoring device 140 (or 140') as shown in FIGS. 10 & 11 (and also FIG. 16), a pedicle screw may be employed of various designs—which may be either of a known design (as described below in relation to FIG. 12, for example) or alternatively may be a novel alternatively modified pedicle screw 130 as shown in FIGS. 9(a) and 9(b). In that alternatively modified pedicle screw 130 its head portion 132 still includes "second interengagement means" formed on or in its radially outer sidewall, but now those "second interengagement means" comprise a circumferential, or alternatively at least one pair of oppositely or diametrically oppositely arranged, externally extending flange(s), lip(s), step(s) or land(s) 132Fa, 132Fb formed in the head portion 132's outer sidewall. Thus, the respective flanged or seating or bearing portions 142a, 142b of the anchoring device 140 can engage with the respective external flange(s), lip(s), step(s) or land(s) 132Fa, 132Fb by virtue of a simple mechanical abutment or seating or bearing relationship.

Figures 6A, 6B:
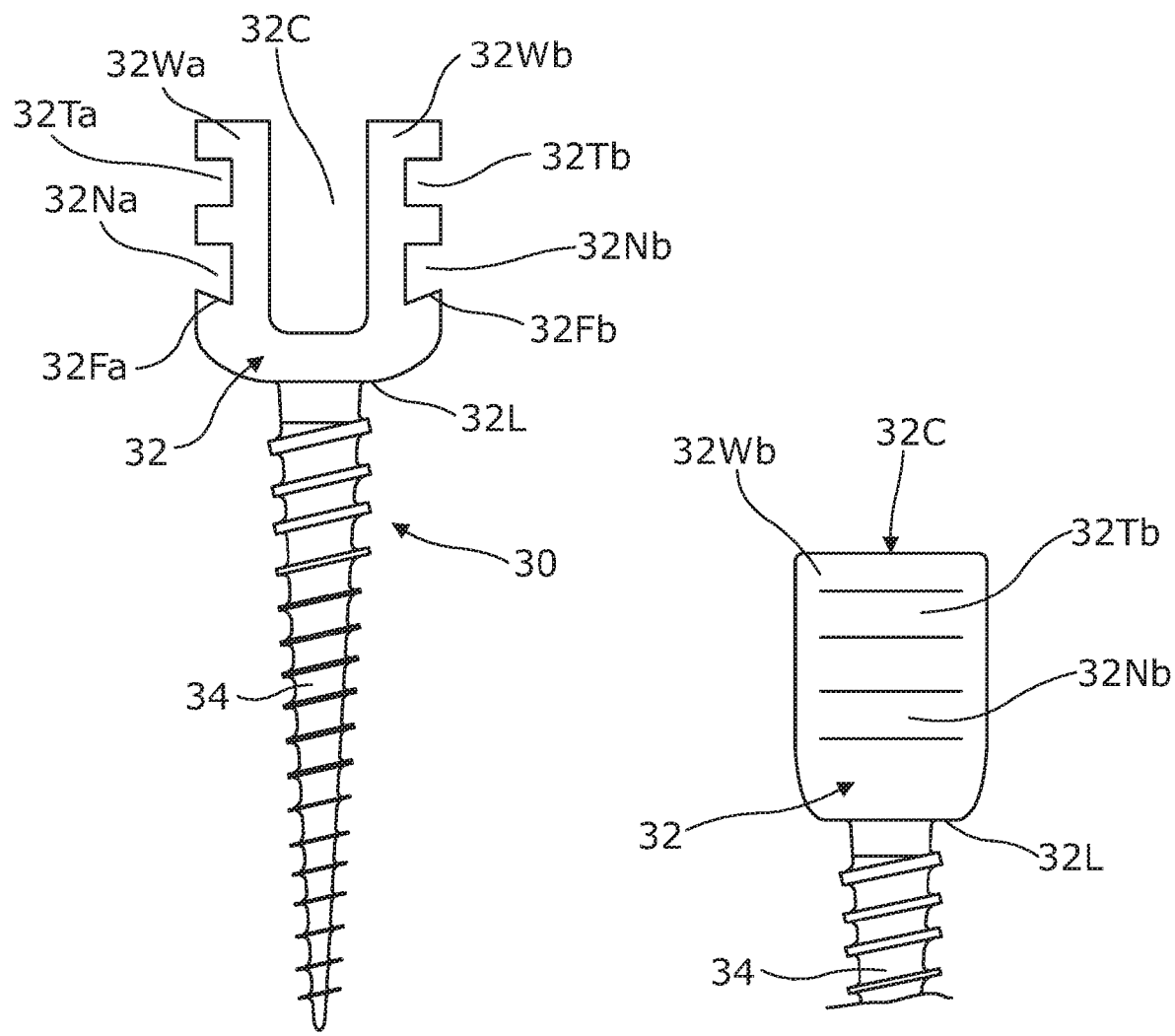
FIG. 6(a) is a frontal view of just the modified pedicle screw shown in FIG. 5(a)
FIG. 6(b) is a side-on view of the head portion of the pedicle screw of FIG. 6(a)
Figures 7A, 7B:
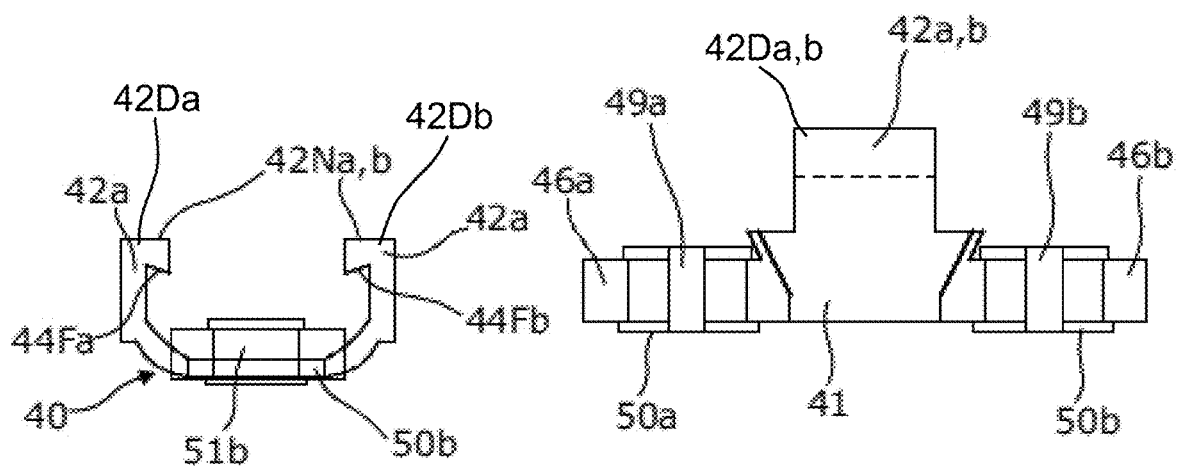
FIG. 7(a) is an end-on view of just the anchoring device show in FIG. 5(b)
FIG. 7(b) is a side-on view of the anchoring device of FIGS. 5(b) and 7(a)
Figures 7C, 7D:
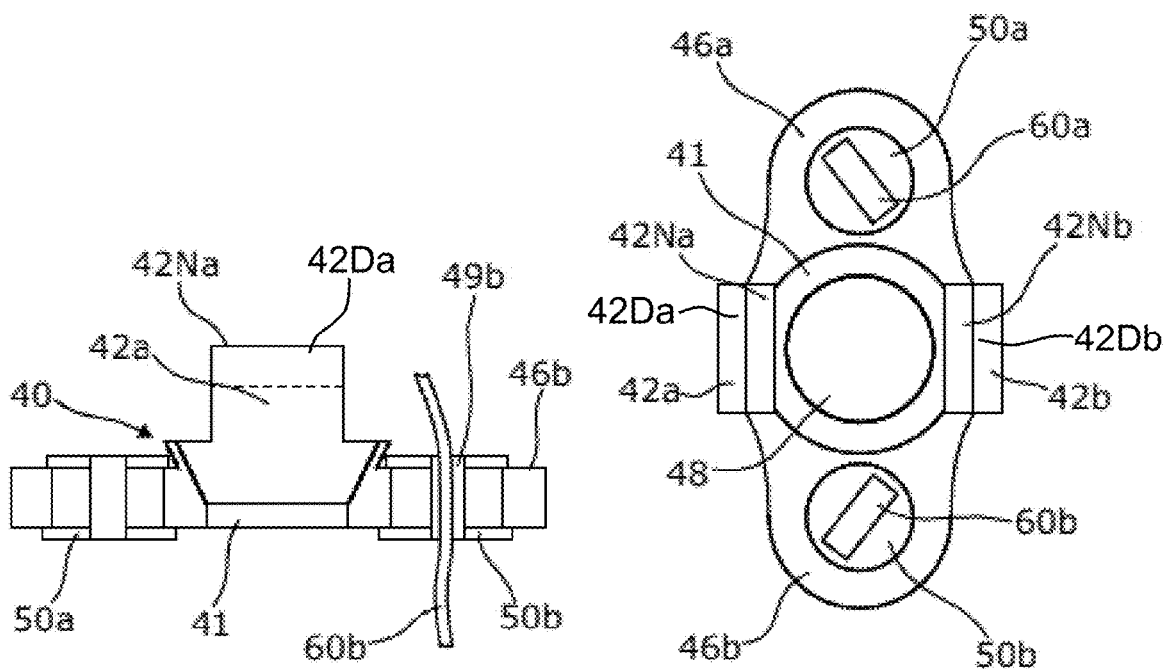
FIG. 7(c) is the same view of the same embodiment anchoring device as in FIG. 7(b), but showing the manner in which a sub-laminar band or tape is passed through one of the inserts located within one of the hoop-like second portions of the device.
FIG. 7(d) is a top plan view of the anchoring device of FIGS. 5(b) and 7(a)-7(c)

The remaining structural features of the alternatively modified pedicle screw 130 of FIGS. 9(a) & 9(b) that are identified by reference numerals not yet referred to as such correspond in form and function to those respective features of the first described modified pedicle screw 30 of FIGS. 6(a) & 6(b) which are referred to by the same basic reference numeral but in the context of the embodiment of FIGS. 9(a) & 9(b) are incremented by 100. Thus, these other labelled structural features in FIGS. 9(a) & 9(b) do not need describing again here.

Figure 12A:
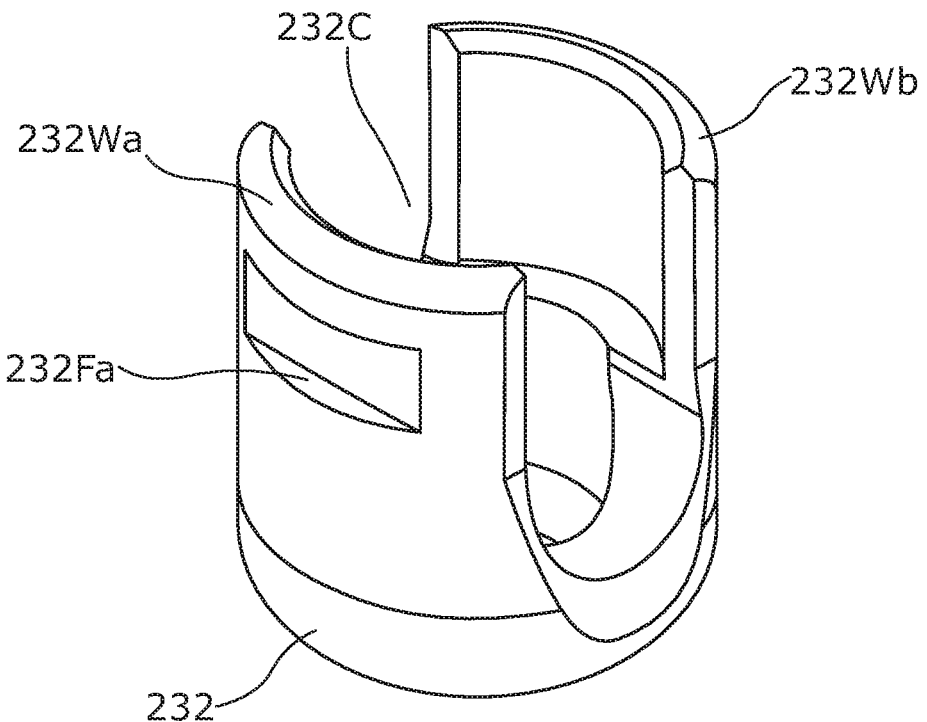
FIG. 12(a) is a perspective view of the head portion of one known design of pedicle screw with which the alternative embodiment anchoring device of FIG. 10 may also be used.
Figure 12B:
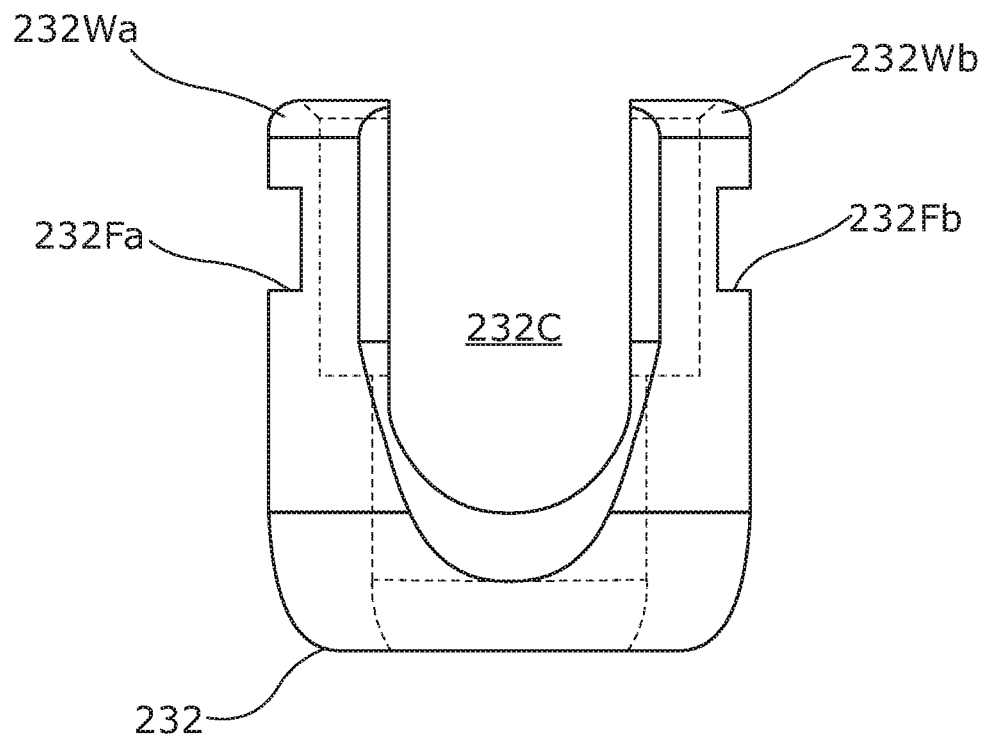
FIG. 12(b) is a side elevational view of the known pedicle screw head portion of FIG. 12(a)

However, the alternative embodiment form of anchoring device 140 of FIGS. 10 & 11 (and also FIG. 16) can also be used in combination with certain known designs of pedicle screw, such as that labelled as 230 whose head portion 232 is shown in FIGS. 12(a) and 12(b). Again, illustrated features of this known pedicle screw head portion 232 which corresponding in form and function to respective features of the first described modified pedicle screw 30 of FIGS. 6(a) & 6(b) are labelled with the same basic reference numeral but incremented by another 100. In this design of pedicle screw head portion 232, the outer sidewalls 232Wa, 232Wb of the body portion of the head portion 232 include a pair of externally facing, diametrically opposed, recesses or recessed lands or indentations or shoulders 232Fa, 232Fb, each of which presents a flat seating or bearing surface on its lower side against which can abut or sit the respective flanged or seating or bearing portions 142a, 142b of the anchoring device 140.

Figure 13:
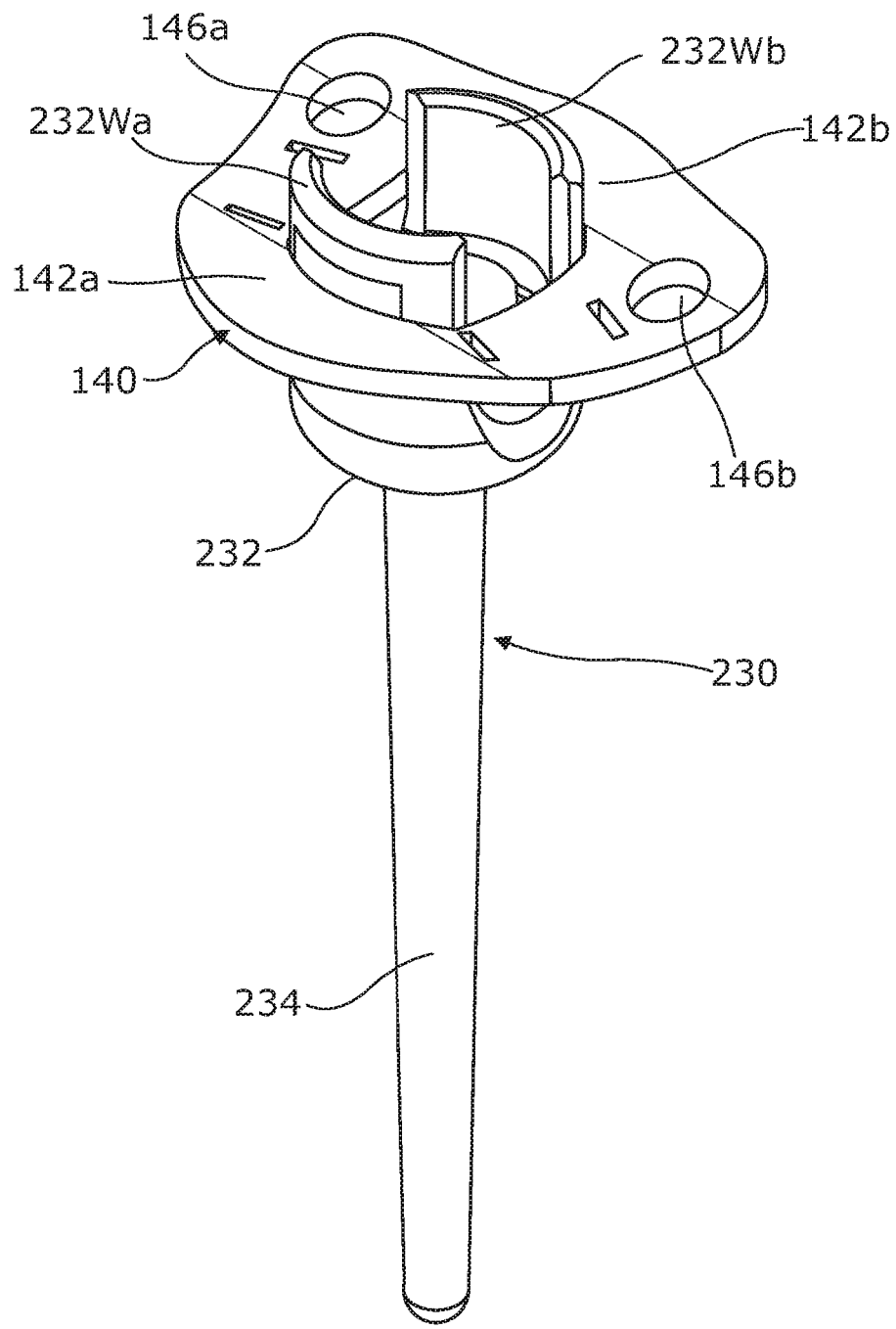
FIG. 13 is a perspective view of the combination of the alternative embodiment anchoring device of FIG. 10 together with the known pedicle screw of FIGS. 12(a) & (b), showing them attached and united together.

FIG. 13 shows the combination of the alternative embodiment anchoring device 140 of FIGS. 10 & 11 together with the known pedicle screw 230 of FIG. 12, showing them in their attached and united condition. As can be appreciated from FIG. 13, the respective flanged or seating or bearing portions 142a, 142b of the anchoring device 140 and the respective recesses or recessed lands or indentations or shoulders 232Fa, 232Fb of the pedicle screw head portion 232 of the screw 230 (or alternatively the external flanges, lips, steps or lands 132Fa, 132Fb of the pedicle screw head portion 132 of the screw 130 of FIG. 9, as the case may be) are overall shaped, dimensioned and positioned relative to each other such that they substantially match or approximate in configuration and fit together with one another in respective pairs thereof such that they can readily unite with each other in a simple abutment or seating or bearing manner, and thus so that the anchoring device 140 and the pedicle screw head portion 232 (or 132) can be readily unitable by virtue of a simple mechanical slide-over or push-fit or friction-fit connection. Moreover, a further advantage of the combined arrangement as shown in FIG. 13 is that the stability of the anchoring device 140 on the screw 230 may come predominantly (or even substantially solely) from the existing geometry of the screw head portion 232. This may thus facilitate use of such an alternative design of anchoring device 140 with existing designs of pedicle screws (e.g. 230), which can lead to lower overall manufacturing costs of new and improved anchoring arrangements provided by embodiments of the present invention.

FIG. 14 shows the attached/united combination of FIG. 13, together with a locking screw K anchoring a stabilising rod 10 extending through the pedicle screw head portion 232, showing the combination ready for receiving various sub-laminar bands or tapes 60a, 60b passing through the various apertures and/or slots/slits thereof.

By way of another practical example only, this time directed specifically to the use of the alternative anchoring device 140 as described in detail above, a summary of the sequence of principal steps used in the deployment of this particular alternative embodiment anchoring arrangement described above may be as follows:

1. The pedicle screw hole is prepared to receive a screw in a standard fashion.
2. The modified screw 130 (or alternatively the known screw 230) is inserted in the usual fashion.
3. The sub-laminar bands 60a, 60b are passed beneath the laminae at the chosen levels.
4. The ends of the bands 60a, 60b are threaded into the anchoring device 140, via the holes and slots/slits 146a, 149a; 146b, 149b, and redundant material is slowly pulled through.
5. As the band tensioning occurs, the device 140 is seated onto the screw head 132 (or 232).
6. Final tensioning of the bands 60a, 60b occurs simultaneously and the tension is maintained by inserting an interference-fit locking/clamping insert T, SC, R etc in the relevant hole/aperture 146a, 146b.
7. The excess band material (if any) is then excised with a blade, leaving e.g. around 5 mm of excess band only.
8. Manipulation of the spine through the screw 130 (or 230) and reduction of the screw 130 (or 230) to the rod 10 may then occur.
9. Once the rod 10 is seated, a locking screw K is secured to the rod 10.
10. Final manipulation and derotation may be performed, as necessary.
11. Final tightening of the locking screw K may occur.

FIG. 15 is a simplified schematic drawing showing one example way in which a sub-laminar band or tape 60a or 60b can be passed through the various apertures/slots/slits of the anchoring device 140 and secured in place therein in order to anchor the band or tape 60a or 60b with respect to a spinal vertebral lamina L during corrective spinal vertebral surgery. The line A→B represents the direction of passage of the band or tape 60a,b as it is threaded through the various apertures/slots/slits of the device 140.

Figure 16:
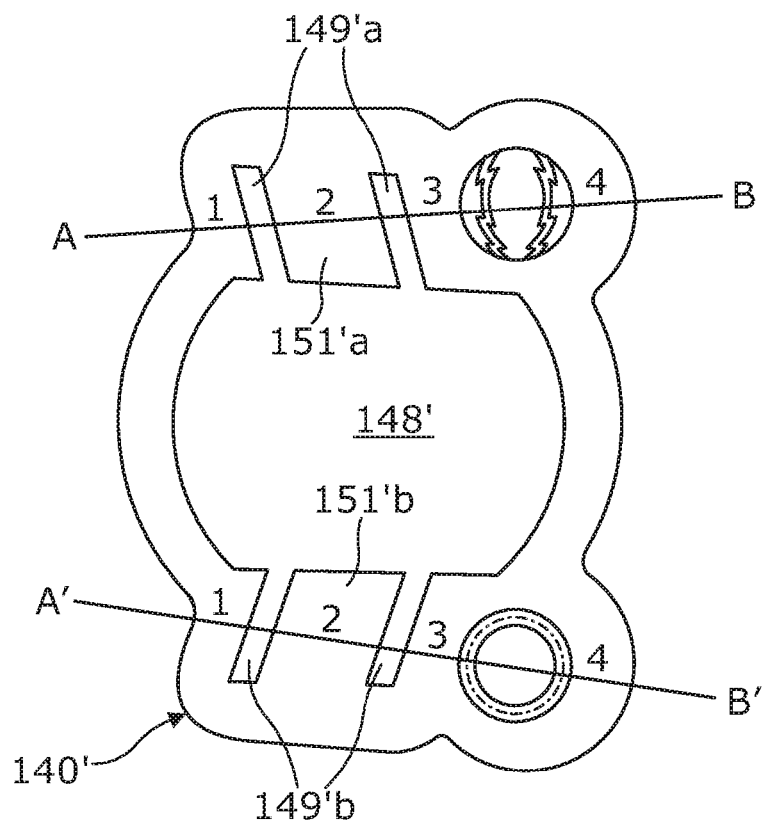
FIG. 16 is a top plan view of a slightly modified embodiment of anchoring device according to the invention, which is very similar to that of FIGS. 10, 11, 13 & 14 but with a slightly different configuration of band/tape anchoring/securement slots.

FIG. 16 shows the slightly modified embodiment of anchoring device 140' with a slightly different configuration of band/tape anchoring/securement slots 149'a, 149'b, as has already been described above.

In order to further explain some of the possible methods for securing the tensioned sub-laminar bands/tapes 60a, 60b to the anchoring device 140' (or even 140), the following two options present themselves, as will now be described with reference to FIGS. 16, 17 and 18:

Once a band/tape 60a,b has been passed beneath the lamina bone L, it needs to be secured to the anchoring device 140', put under appropriate tension and then locked in place with that tension. These steps may be carried out as follows:

(i) Band passage:
   (a) Option 1 (referring to FIGS. 16 & 17—and following the direction of line A→B):
      The band is looped through the various apertures/slots/slits as per FIG. 17.
   (b) Option 2 (referring to FIGS. 16 & 18—and following the direction of line A'→B'):
      One limb of the band/tape 60a,b is looped through the various apertures/slots/slits in a similar way to Option 1 moving from A towards B. In this Option 2, however, the last section of the anchoring device 140' (annotated "4" in these FIGS.) is machined to be circular in cross-section (FIG. 18). The limb of the band/tape 60a,b in this situation is passed twice through the large hole/aperture 146'a,b.

(ii) Band tensioning:
   (a) Option 1 (referring to FIGS. 16 & 17—and following the direction of line A→B:
      Once the band/tape 60a,b is fully passed, it is tensioned manually and then with a tensioning device, to maintain the desired tension. A screw SC is inserted into the largest of the holes/apertures 146'a,b which causes a crimping of the band/tape material in order to securely hold the band/tape 60a,b in its tensioned position (FIG. 17).
   (b) Option 2 (referring to FGS. 16 & 18—and following the direction of line A'→B':
      Because of the smooth circular finish to section "4" of the device 140', the limb of the band/tape 60a,b is still amenable to manual tensioning, despite it being looped around the device 140'. Once manual tensioning is achieved, final tensioning occurs with a tensioning device which holds the desired tension. A Rawlplug-like screw insert or anchor R is inserted into the largest hole/aperture 146'a,b from above, and a ~2 mm screw SC inserted to definitively secure the tension in the band/tape 60a,b.

(iii) Once tensioning is secured, the bands/tapes are cut ~5 mm from the securing interfaces.

It is to be understood that the above description of some specific embodiments of the invention in terms of their various features and aspects has been by way of non-limiting example(s) only, and various modifications may be made from what has been specifically described and illustrated whilst remaining within the scope of the invention as set out in the appended claims.

Throughout the description and claims of this specification, the words "comprise" and "contain" and linguistic variations of those words, for example "comprising" and "comprises", mean "including but not limited to", and are not intended to (and do not) exclude other moieties, additives, components, elements, integers or steps.

Throughout the description and claims of this specification, the singular encompasses the plural unless expressly stated otherwise or the context dictates otherwise. In particular, where the indefinite article is used, the specification is to be understood as contemplating plurality as well as singularity, unless expressly stated otherwise or the context dictates requires otherwise.

Furthermore, through this specification any feature, component, element, integer, characteristic, property, compound, chemical moiety or group described in conjunction with a particular aspect, embodiment or example of the invention is/are to be understood to be applicable to any other aspect, embodiment or example described herein unless incompatible therewith or expressly stated otherwise.

The invention claimed is:

1. An anchoring device for anchoring one or more sub-laminar bands or tapes to a pedicle screw, the device comprising:
    a first portion configured for attachment to a head portion of the pedicle screw by interengagement with said head portion; and
    a plurality of second portions for anchoring thereto one or more sub-laminar bands or tapes;
    wherein the first portion includes first interengagement means for interengagement with the head portion of the pedicle screw to effect the said interengagement attachment of the first portion of the anchoring device thereto;
    wherein the said plurality of second portions are arranged equi-angularly or symmetrically around the first portion of the device, each second portion being configured and arranged for anchoring thereto a said sub-laminar band or tape, and each said second portion including, or being configured as, an apertured or hollow hoop- or loop-like portion or extension located on or extending from diametrically opposite sides of the first portion of the device and extending in radially opposite directions therefrom,
    and further wherein each of the second portions has a general plane in which it lies and the second portions are configured such that the respective general planes of the second portions are substantially co-planar with each other.

2. An anchoring device according to claim 1, wherein the first portion is configured for attachment to the head portion of the pedicle screw by interengagement of the first interengagement means with a radially outer sidewall portion of the screw head portion.

3. An anchoring device according to claim 2, wherein the first portion is configured such that, upon interengagement of the first interengagement means with the outer sidewall portion of the screw head portion, at least a lower part of the first portion of the device adjacent the first interengagement means abuts or lies adjacent or engages a lower sidewall portion of the screw head portion.

4. An anchoring device according to claim 1, wherein the first portion of the device is configured such that it is attachable to the head portion of the pedicle screw, via the interengagement therewith of the first interengagement means, by means of insertion of a screw-threaded shaft of the pedicle screw, which shaft extends from a base of the head portion, through an aperture in the first portion of the device in a direction away from the first portion of the device and relative movement towards one another of the first portion of the device and the base of the screw head portion.

5. An anchoring device according to claim 1, wherein the first portion comprises an apertured or hollow base portion and one or more attachment portions extending generally perpendicularly therefrom.

6. An anchoring device according to claim 5, wherein (ii) is satisfied, and each interengagement nose portion includes an obliquely inclined interengagement surface therebeneath, wherein either:
    (a) the angle of inclination of each respective interengagement surface is such that a radially inner end of each respective nose portion is closer to the base portion of the first portion of the device than is a radially outer end of the respective nose portion; or
    (b) each interengagement nose portion comprises a lower interengagement surface, which is that surface directed towards the base portion of the first portion of the device, which forms an angle of less than 90 degrees, with a radially inner side surface of the respective attachment portion to which the respective nose portion is joined.

7. An anchoring device according to claim 5, wherein (ii) is satisfied, and the respective interengagement nose portions of the pair of attachment portions form a snap-fit attachment mechanism with the second interengagement means on the head portion of the pedicle screw.

8. An anchoring device according to claim 5, wherein either one or both of the following (i) and (ii) is/are satisfied:
    (i) wherein the attachment portions are configured as a pair of diametrically oppositely arranged protruding lugs, tabs or arms extending perpendicularly from the base portion on diametrically opposite sides thereof, and are disposed so as to be generally substantially parallel to one other and configured to interengage with the outer sidewall of the head portion of the screw on diametrically opposite sides of the screw head portion;
    (ii) wherein the attachment portions each terminate at a distal end thereof (that being the end thereof opposite a proximal end thereof at which the respective attachment portion is joined to the base portion of the first portion of the device) in a radially inwardly projecting interengagement nose portion, whereby the interengagement nose portions of the pair of attachment portions point generally towards one another from opposite sides, especially diametrically opposite sides, of the first portion of the device.

9. An anchoring device according to claim 1, further wherein the second portions are configured such that the respective general planes of the second portions are substantially co-planar with a general plane of a base portion of the anchoring device from which extend the first interengagement means which provide the interengagement attachment of the first portion of the device to the pedicle screw head portion.

10. An anchoring device according to claim 1, wherein each of the second portions has mounted therein an insert for providing the means of anchoring to that second portion of the device the or the respective sub-laminar band or tape;
    and wherein the or each insert comprises a central body, in which there is provided a slot or aperture through which is able to pass or be accommodated the or the respective sub-laminar band or tape, and an outer frame configured for mounting the insert in the respective second portion of the device.

11. An anchoring device according to claim 10, wherein either one or both of the following (i) and (ii) is/are satisfied:
    (i) wherein the central body of the or the respective insert takes the form of a short circular cylinder, which is mounted freely rotatably within a geometrically similar circular mounting within the respective frame, so that the orientation of the slot or aperture therein may vary or be self-adjusting so as to adopt an optimum orientation as dictated by the various forces that may be exerted on the anchoring device by the one or more sub-laminar bands or tapes once they have been anchored to the device and tightened into their desired secured or locked condition;

(ii) wherein either:
  (a) the slot or aperture within the respective central body of each respective insert is dimensioned to allow the respective sub-laminar band or tape to pass and slide freely therethrough, and a separate discrete securement or locking device is provided for securing the respective sub-laminar band or tape in its tightened condition once it has been deployed in its desired configuration having been passed or threaded around the relevant vertebra (e) and anchored to the anchoring device; or
  (b) the or each respective slot or aperture within the respective central body of the respective insert itself includes a securement or locking device which allows the respective sub-laminar band or tape to be secured directly within the respective insert of the device.

12. An anchoring device according to claim 10, wherein the or each outer frame is configured to be engageable in the respective second portion of the device by means of a respective snap-fit connection.

13. An anchoring device according to claim 1, wherein the first portion of the device is configured such that it is attachable to the head portion of the pedicle screw, via the interengagement therewith of the first interengagement means, by means of placement of a hole or aperture in the first portion of the device over the pedicle screw's head portion from thereabove, i.e. from the side thereof opposite to that from which extends the pedicle screw's threaded shaft, and the anchoring device and the head portion of the pedicle screw are attachable and unitable by virtue of a push-fit or friction-fit or abutment-fit connection.

14. An anchoring device according to claim 13, wherein any one or more of the following (i), (ii) and (iii) is/are satisfied:
  (i) wherein the anchoring device is formed as a substantially unitary one-piece structure, and is configured with at least one portion thereof curved or bent or concave or convex or ramped or stepped with respect to the remainder of the device;
  (ii) wherein the first interengagement means comprises at least one pair of oppositely or diametrically oppositely arranged, flanged or seating or bearing portions of the device;
  (iii) wherein each second portion of the device comprises one or more, or a plurality of, holes or apertures or slots or slits formed in and/or extending through the material of the respective second portion.

15. An anchoring device according to claim 14, wherein (iii) is satisfied, and wherein:
  either (a) the defining perimeter(s) of any one or more of the said hole(s)/aperture(s) or slots/slits is/are wholly contained within the material of the relevant second portion of the device in which it/they is/are formed;
  or (b) the defining perimeter(s) of any two of the said hole(s)/aperture(s) or slots/slits is/are only partially contained within the material of the relevant second portion of the device in which they are formed, so that the relevant hole(s)/aperture(s) or slots/slits is/are open and unbounded on at least one side or portion thereof, thereby creating a or a respective tab or tongue ibetween at least one pair thereof.

16. An anchoring arrangement for anchoring one or more sub-laminar bands or tapes with respect to one or more spinal vertebrae in corrective spinal vertebral surgery, the arrangement comprising:
  a pedicle screw for insertion into a selected vertebral pedicle; and
  an anchoring device according to claim 1.

17. An anchoring arrangement according to claim 16, wherein the head portion of the pedicle screw comprises second interengagement means configured for interengagement with the first interengagement means provided on the first portion of the anchoring device, whereby the first and second interengagement means are each configured so that they together, once they are interengaged with each other, effect the said attachment of the first portion of the anchoring device to the head portion of the pedicle screw.

18. A kit or set of component parts, comprising:
  at least one pedicle screw for insertion into a selected vertebral pedicle of one or more spinal vertebrae; and
  at least one anchoring device according to claim 1.

19. A kit or set according to claim 18, further comprising one or more sub-laminar bands or tapes.

* * * * *